US008642749B2

(12) United States Patent
Streatfield et al.

(10) Patent No.: US 8,642,749 B2
(45) Date of Patent: Feb. 4, 2014

(54) REGULATORY REGION PREFERENTIALLY EXPRESSING TO SEED EMBRYO AND METHOD OF USING SAME

(75) Inventors: Stephen J Streatfield, Kennett Square, PA (US); Robert Love, Bryan, TX (US); Jeff Bray, Bryan, TX (US)

(73) Assignee: Applied Biotechnology Institute, San Luis Obispo, CA (US)

( * ) Notice: Subject to any disclaimer, the term of this patent is extended or adjusted under 35 U.S.C. 154(b) by 507 days.

(21) Appl. No.: 12/901,513

(22) Filed: Oct. 9, 2010

(65) Prior Publication Data

US 2011/0091976 A1   Apr. 21, 2011

Related U.S. Application Data

(60) Provisional application No. 61/253,469, filed on Oct. 20, 2009.

(51) Int. Cl.
C07H 21/04 (2006.01)
C12N 15/82 (2006.01)
C12N 15/87 (2006.01)
C12N 15/00 (2006.01)
A01H 9/00 (2006.01)

(52) U.S. Cl.
USPC ....... 536/24.1; 435/468; 435/419; 435/320.1; 800/287; 800/295

(58) Field of Classification Search
None
See application file for complete search history.

(56) References Cited

U.S. PATENT DOCUMENTS 7,081,566 B2 * 7/2006 Abbitt et al. ................... 800/287
7,321,031 B2 * 1/2008 Abbitt et al. ................. 536/24.1

OTHER PUBLICATIONS

Komarnytsky and Borisjuk, Genetic Engin 25:113-41 (2003).*
GenBank Accession No. AC214363.4 "*Zea mays* BAC clone CH201-186G11 from chromosome 5, complete sequence," Nov. 14, 2007.
GenBank Accession No. BT038630.1 "*Zea mays* full-length cDNA clone ZM_BFb0298I19 mRNA, complete cds," Jul. 30, 2008.
GenBank Accession No. ZM_BFb0298I19 "*Zea mays* full-length cDNA clone ZM_BFb0298I19 mRNA, complete cds," Jul. 30, 2008.
GenBank Accession No. EU941551.1 "*Zea mays* clone 1460842 mRNA sequence," Aug. 4, 2008.
GenBank Accession No. EU940752.1 "*Zea mays* clone 1061963 mRNA sequence," Aug. 4, 2008.
GenBank Accession No. BT084022.1 "*Zea mays* full-length cDNA clone ZM_BFb0066F20 mRNA, complete cds," May 23, 2009.
GenBank Accession No. NM_001154561.1 "*Zea mays* ZFP16-2 (LOC100281642), mRNA," Apr. 11, 2009.
GenBank Accession No. NM_001152370.1 "*Zea mays* hypothetical protein LOC100279352 (LOC100279352), mRNA," Apr. 11, 2009.
GenBank Accession No. NM_001147188.1 "*Zea mays* hypothetical protein LOC100272735 (LOC100272735), mRNA," Apr. 11, 2009.

(Continued)

Primary Examiner — Shubo (Joe) Zhou
Assistant Examiner — Russell Boggs
(74) Attorney, Agent, or Firm — Patricia Sweeney

(57) ABSTRACT

A *Zea mays* regulatory region is shown, which provides improved seed preferred, and particularly embryo preferred expression in plants. Methods of use are also shown in preferentially expressing a heterologous protein to the embryo tissue of a plant. The sequence is particularly useful in expression of heterologous proteins to the embryo of monocotyledonous plants, particularly cereals, and maize.

16 Claims, 4 Drawing Sheets

(56) References Cited

OTHER PUBLICATIONS

GenBank Accession No. BT024168.1 "*Zea mays* clone EL01N0323B09 mRNA sequence," Oct. 2004.
GenBank Accession No. EU974988.1 "*Zea mays* clone 462361 mRNA sequence," Aug. 4, 2008.
GenBank Accession No. AAB23306 "MBP-1=small, acid-soluble, basic anti-microbial peptide [*Zea mays*=maize, inbred B73, seeds, Peptide, 33 aa]," Sep. 15, 1992.
Streatfield, et al. (2010) "Identification of maize embryo-preferred promoters suitable for high-level heterologous protein production," GM Crops 1:3, 162-172.
NCBI BLAST, Oct. 4, 2009.

* cited by examiner

Figure 1

```
tcctcctgctcccctcctacctctggtggaccatcgaccgcgcccggctccggtgcctgcaccgcacgcc
acatgcggccgatgggcagcggaagctagcagcccggcttgaatgacctatattatatgaagaagatgcc
tcagatgctactcgactacaaggtttatgtttctcaggtgactaaatagatcatgtgctgatgttagcga
ttcttgtgtggaagtgaattcatgccaatttgaagccaatatggtttaggtgtattttttactggattta
ggttgaaggtcaatttgtcttctttttattctgcaaatacacattgacaacctaatgactttctattgtt
ttaatatcagaccaataaaccttttttcttttttttaatatgctatgaactgtatcagctttgtgacctct
tgtttccatttcccccttggattcatataattaactttcgacaccagagcaatacatctgtcatcaattat
taacataatatgttatgtcttgcttggtttagcctcaagaggttttatgcatgttcttttgtattgcttg
gggtgttaactttttttatccatttggtgtgggtgagggtgggatctgttattcctgatgtaatgcataa
tccattcattatgatcatagtaggaatatggctacactgactcttcttcctcagtggagtacaattggt
ggccttatatacttgatgtgggcgtcattttacgattgcctctgaatgtgggagtagtcttatggtaat
aaaagtcaaacaattctaatgtgttgtgctagatctaaattaccttgaagacattgttggggttccaat
gtcactgttgacatcatatccaaatttgtatccttctgtatggtgtgatatatctagaagctctaagaat
ttttgtcttgtgcaggtcctgtaattaatgaatgatttgaaccaaagtgttcgaggtactgttctcttgt
attgaggttagttaattccatatttgatactctataggcctactttagttgacattttgatttttttccac
acccataatgactggtgtgatatctatttccattgatcttgttcaatttcccaatagttacatcctacat
ttacaacctggagagattgaagcatttttatagcaacatctgaactattaaaactcaccgtttgctccac
cacgggcttaggttcttcgacctctctatgaatcccccctaagataccagaactgttgtagtggttatata
tattgagtatctgtttgaattgtaagaccttgtgatatttccagaagatttgtataagtctgtaatttgt
tgtgataatattagcatctaaatgatgcaattgatataacattattaaaatcataaatagaagtttgcat
ggtaccgatggttgcaatgtagtggtgaaataactatattaaaataacaaaatgtatgtatggctagcta
ggatttataaaatcttttcttataacacatatttgtatataaattatcatgatattatatgttcccgtt
gcaacgcacgggcacttatatatatatgtgtgtgttttttttttcacatgtacccatcagataggatg
ataagagaggttaaatcatgccttaaggaacatcttaagaagtgtttttacatgctacattttggtggat
tttatataaccgttttttacatacatacggccctatatatatcatagttcagtttgattcctccgttaca
aaccaactaaatgcatagaccacgcggaccgaaagcaacagggtcgatgagtcgaagcagcggggccgat
gaagtcgaagcggtctcctgaacgcagatgcacgtcggcgatcggatggctgggatggcgacgcagttg
tgagtagaggcgaaaacttaatttgtgttgggattgacactaggcgccttatatagggccgtgtccacga
accgataacgatgcgcgatccgatctacacgttatccacgaatcgatagactcgcgttccgttcatatcc
ttatcgggatcggttagggctctaaaattaacagccaagcaacagcctcggcccggcgaggcgagcgcgt
gtggttctccacactctctcctctcatccatgacttggtgagtgagcgtagcatccatatttaaactagt
tccactccacttgaactagcaatatgacactatttgtttcaccattctctagccataccatacatgcgct
tttgagatttttttaggatttaattgaatttctcaattgggcctatcccataaatccaacacgatataag
tctatctgtcgctggtagattgagagatgatgtgtgcatgtctgtaaataaaaaaattgcttttacaca
taaattgcgctatgactttacatgaaataaattttctaaaatttaaaacttacataagtaaaaaaatat
aaagaaggaagaaacacgacatggaaaaaaatctctcgttgttttatatggaggcaacggctgcagtcc
ccgtgcaagcgatgctcatccgttcccatggcgtgcacggcccagaaacgacacgcttcacctacttctt
ccctgccaccacacccaccgtccacccacaccacaccgcgcgccacgcgcccacggcacctcggcacagt
gtcgtcgcatgtcgctcacgtactgtcgcagaactcacaccgtcacacggtgcctgctatctagctaatg
ctgctagcagccatgtcacaccgatataacccggccaccgcgcgccgcgccacgtcgccatgcacgcggc
cacgtccccgatcgatcgacgtcgtcctcctcatcctggctcctccattcccgcgcttctataaatacct
cggccatgtacatcgacccagccatctcctcaccctcgttcaccacacagcccgccactcctttagtagc
ttgtgatttgtacgtcgacgagatcactggttggcggacgacgacccatg
```

REGULATORY REGION PREFERENTIALLY EXPRESSING TO SEED EMBRYO AND METHOD OF USING SAME

REFERENCE TO RELATED APPLICATIONS

This application claims priority to previously filed and co-pending application U.S. Ser. No. 61/253,469, filed Oct. 20, 2009, the contents of which are incorporated herein in their entirety.

SEQUENCE LISTING

The instant application contains a Sequence Listing which has been submitted in ASCII format via EFS-Web and is hereby incorporated by reference in its entirety. Said ASCII copy, created on Oct. 20, 2010, is named AB00012.txt and is 8,476 bytes in size.

BACKGROUND OF THE INVENTION

Promoters are vital molecular tools that have been applied widely in plant biotechnology to control the expression of introduced genes. There are many applications for promoters in driving gene expression in plant tissues. These include the synthesis of scoreable and selectable markers to identify transgenic plants (Jefferson et al., 1987; Wohlleben et al., 1988) and the over-expression of control point enzymes to modify metabolic flux through key pathways, so affecting the yields of important plant products (Nessler, 1994; Lessard et al., 2002). Other uses of plant promoters include the expression of genes conferring resistance to pests, thus conferring protection (Estruch et al., 1997), and the expression of non-native enzymes to facilitate the production of foreign metabolites in particular plant species (Poirier et al., 1995; Ye et al., 2000). A further application of plant promoters is to over-express controlling regulatory genes affecting aspects of plant physiology such as flowering time and so modify plant growth characteristics (Weigel and Nilsson, 1995). Promoters are also used to repress the expression of specific genes by driving the synthesis of interfering RNA species (Waterhouse et al., 2001), thus affecting plant metabolic and developmental pathways (Yu and Kumar, 2003). Although high levels of expression may not be necessary for all of the above applications, there is clearly a need for promoters showing activity in plant tissues.

Apart from these and other applications of promoters to modify plant traits, promoters are also required for plants to act as production systems for heterologous proteins. Plants have been used to produce a wide range of recombinant proteins of potential economic and/or medicinal importance. These include research chemicals (Hood et al., 1997; Zhong et al., 1999), processing enzymes that are used, for example, in the pharmaceutical industry (Woodard et al., 2003), industrial enzymes that are deployed in large-scale processing operations such as bleaching (Hood et al., 2003; Bailey et al., 2004), candidate vaccine antigens for animal or plant disease prevention (Mason et al., 1992; Haq et al., 1995; Carrillo et al., 1998; Streatfield et al., 2001; Streatfield et al., 2003), and therapeutic pharmaceuticals including antibodies (Daniell et al., 2001; Hood et al., 2002). The expressed proteins may either be purified from the plant tissues (Hood et al., 1997; Woodard et al., 2003) or, if as with vaccines the final application allows it, the recombinant plant material may be processed into a suitable form for use or even deployed directly (Streatfield et al., 2002; Lamphear et al., 2002). For these and other protein products to be produced in plant systems it is necessary that promoters drive a sufficiently high level of expression to ensure commercial viability.

Spatial and temporal control is also often important in driving gene expression in plants. For example, selectable and scoreable markers must be expressed at a suitable time and in an appropriate tissue to allow for screening, and controlling enzymes and regulatory factors must be produced in metabolically active and physiologically responsive tissues, respectively. Similarly, genes conferring host protection must be expressed in the target tissues for the pathogen or pest, and plant produced protein products should be expressed in tissues suitable for protein accumulation and storage. Furthermore, since certain protein products may have detrimental effects on plant health and yield when expressed in metabolically active plant tissues that are essential for survival and growth, promoters may be favored that are active in the chosen plant storage tissues but show low or no activity in other, non-storage tissues.

Promoters that preferentially express relatively high levels of foreign proteins in tissues suitable for stable protein accumulation and storage are particularly useful for commercial protein production. The seed tissues of the cereals are especially well suited to the large-scale production of recombinant proteins. Thus, there is a requirement for promoters that show a seed tissue preferred expression pattern in plants and particularly cereals and drive relatively high levels of protein accumulation in these tissues.

Several promoters of plant and plant pathogen (bacterial and viral) origin have been used to direct transgene expression in plants. Prominent examples include the French bean beta-phaseolin promoter (Bustos et al., 1989), the mannopine synthase promoter of *Agrobacterium tumefaciens* (Leung et al., 1991), and the 35S promoter of cauliflower mosaic virus (Guilley et al., 1982). These and several other promoters in widespread use in plants were originally developed and utilized in dicot species. Promoter sequences from one species are predictably used in other species (see discussion below). The cereals comprise particularly important crops and there is therefore a pressing need for promoters that have high activity and/or tissue preference in monocots. Cereals, such as grasses, are cultivated for their grain. Since the nutritional value of cereals is in their seeds, and these tissues are also well suited for recombinant protein accumulation and storage, promoters that are active in cereal seed tissues are especially useful.

Two broad classes of promoters are typically deployed: constitutive and tissue preferred. Constitutive promoters, such as maize polyubiquitin-1 drive expression in the seed but also in other tissues (Christensen et al., 1992). A drawback with such constitutive promoters is that expression in tissues other than seed storage tissues may result in plant health being compromised, for example if a potentially toxic protein is expressed in metabolically active tissues required for germination or growth (Hood et al., 2003). Furthermore, constitutive expression may result in the expressed foreign protein being synthesized in pollen grains and thus being difficult to contain. By contrast, seed preferred promoters limit all or the bulk of transgene expression to seed tissues, so avoiding such concerns. Tissue preferred expression can include seed preferred expression. An example of one such promoter providing seed preferred expression is the phaseolin promoter. See, Bustos et al. "Regulation of β-glucuronidase Expression in Transgenic Tobacco Plants by an A/T-Rich cis-Acting Sequence Found Upstream of a French Bean β-Phaseolin Gene" The Plant Cell Vol. 1, 839 853 (1989).

The principle tissue types in maize seeds are the embryo, the endosperm including a surrounding aleurone cell layer and the maternally derived pericarp. Of these, the endosperm and to a lesser extent the embryo, comprise most of the volume of the seed. Thus, endosperm and embryo promoters are particularly important for modifying seed characteristics and contents. The proximal 1.1 kb of a maize 27 kD γ-zein promoter (Russell and Fromm, 1997), the proximal 1.45 kb of a maize globulin-1 promoter (Belanger and Kriz, 1991; Genbank accession L22344) and the proximal approximately 3 kb of a maize globulin-2 promoter (U.S. Pat. No. 7,112,723) are prominent examples of seed preferred promoters that have been used to express transgenes in the seeds of monocots.

However, despite these examples, there is currently a very limited repertoire of promoters for preferentially expressing foreign proteins in the seed tissues of plants, and in particular, cereals. There is a need for further promoters that express transgenes at similar or higher levels to those currently deployed and with similar or improved tissue specificity. The best promoters would facilitate the expression of foreign proteins in seeds at higher levels than are currently achieved, while restricting expression specifically or predominantly to seed tissues. Also, a range of new promoters would allow the expression of multiple copies of a single transgene in seeds without the need to repeatedly use the same promoter. This should reduce silencing phenomena associated with promoter methylation (De Wilde et al., 2000), and thereby it should also serve to boost expression. Similarly, multiple distinct transgenes could be simultaneously expressed from different promoters in seed tissues, allowing more complex traits and foreign protein products to be reliably introduced into seeds.

All references cited herein are incorporated herein by reference.

SUMMARY OF THE INVENTION

A *Zea mays* embryo regulatory region has been identified and has preferential expression to the embryo of a plant. This invention describes a sequence with improved preferential transgene expression in plant embryo tissues. In an embodiment, it is used to drive expression preferentially to embryos in monocotyledonous plants, particularly cereal plants, and most preferentially, in maize.

DESCRIPTION OF THE DRAWINGS

FIG. 1 shows the nucleotide sequence (SEQ ID NO: 1) of the regulatory region of the invention and the putative TATA box underlined, based on the consensus sequence and where combined with the ATG start site (marked in bold) it is SEQ ID NO: 2.

DESCRIPTION OF THE PREFERRED EMBODIMENTS

Figure 2:
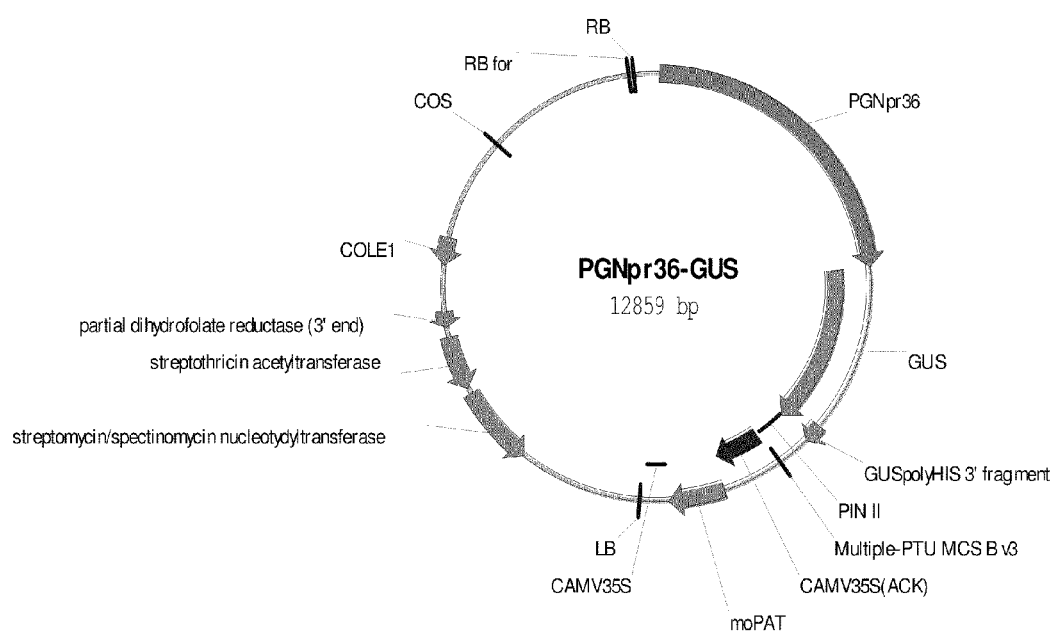
FIG. 2 shows a vector map of a construct with the ZM embryo promoter PGNpr36 fused to GUS with a pinII terminator in a vector designed for *Agrobacterium* transformation with a left border (LB) and right border (RB) of *Agrobacterium*, the 35S promoter driving the maize optimized phosphinothricin marker gene (moPAT) and 35S terminator and bacterial genes for *Agrobacterium* selection

Nucleotide sequences are described herein that regulate transcription with preferential expression to plant seed tissue, and preferential expression to plant embryo tissue in the seed. These novel nucleotide sequences are to a *Zea mays* embryo-preferred regulatory region designated also as PGNpr36.

A genomics approach can be used and is described to identify further sequences that can drive high levels of transgene expression in maize embryo tissues. The promoter sequence is shown in FIG. 1 as the sequence up to the ATG start site and is SEQ ID NO: 1. Together with the ATG start site, indicated in bold, it is SEQ ID NO: 2. It is an 2987 base pair/2990 (with ATG start site) sequence and includes a leader sequence. Transgenic plants generated using this sequence show expression from 12 days after pollination onward through at least 21 days post harvest.

Thus, this new ZM embryo-preferred promoter is well suited to drive transgene expression in plant seeds. The here cloned promoter is particularly useful for the expression of gene sequences in cereal plants and especially in maize plants. However, it can be used in any plant species, including, for example, a monocotyledonous plant such as wheat, rye, rice, oat, barley, turfgrass, sorghum, millet or sugarcane. Alternatively, the plant may be a dicotyledonous plant, for example, tobacco, tomato, potato, soybean, cotton, canola, sunflower or alfalfa. Maize promoters have been used repeatedly to drive expression of genes in non-maize plants, including tobacco (Yang and Russell, 1990; Geffers et al., 2000; Vilardell et al., 1991), cultured rice cells (Vilardell et al., 1991), wheat (Oldach et al., 2001; Brinch-Pedersen et al., 2003), rice (Cornejo et al., 1993; Takimoto et al., 1994), sunflower (Roussell et al., 1988) and protoplasts of carrot (Roussell et al., 1988).

The nucleotide sequences of the invention can be used to isolate corresponding sequences from other organisms, particularly other plants, more particularly other monocots, or to synthesize synthetic sequences. In this manner, methods such as PCR, hybridization, synthetic gene construction and the like can be used to identify or generate such sequences based on their sequence homology to the sequences set forth herein. Sequences identified, isolated or constructed based on their sequence identity to the whole of or any portion of the ZM embryo promoter set forth herein are encompassed by the present invention. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook et al., 1989; Innis et al., 1990; Innis et al., 1995; Innis et al., 1999). Known methods of PCR include, but are not limited to, methods using paired primers, nested primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989).

For example, the ZM embryo promoter disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20.times.SSC=3.0 M NaCl/0.3 M trisodium citrate) at 50 to 55° C. Exemplary moderate stringency conditions include hybridization in 40 to 45% formamide, 1.0 M NaCl, 1% SDS at 37.degree. C., and a wash in 0.5× to 1×SSC at 55 to 60.degree. C. Exemplary high stringency conditions include hybridization in 50% formamide, 1.0 M NaCl, 1% SDS at 37° C., and a wash in 0×SSC at 60 to 65° C.

Specificity is also the function of post-hybridization washes, the critical factors being the ionic strength and temperature of the final wash solution. For DNA-DNA hybrids, the $T_m$ can be approximated from the equation $T_m=81.5°$ C.$+16.6$ (log M)$+0.41$(% GC)$-0.61$(% form.)$-500/L$, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Ausubel et al. (1993) and Sambrook et al. (1989).

Thus, isolated sequences that have promoter activity and which hybridize under stringent conditions to the promoter sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988), the local homology algorithm of Smith and Waterman (1981), the homology alignment algorithm of Needleman and Wunsch (1970), the search-for-similarity-method of Pearson and Lipman (1988) and the algorithm of Karlin and Altschul (1990), modified as in Karlin and Altschul (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif., USA); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins and Sharp (1988), Higgins and Sharp (1989), Corpet (1988), Huang et al. (1992) and Pearson (1994). The ALIGN program is based on the algorithm of Myers and Miller (1988). The BLAST programs of Altschul et al. (1990) are based on the algorithm of Karlin and Altschul (1990). To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules, see Altschul et al. (1997). When utilizing BLAST, Gapped BLAST or PSI-BLAST, the default parameters of the respective programs (e.g. BLASTN for nucleotide sequences, BLASTX for proteins) can be used, see the World Wide Web site ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an identical or similar alignment of nucleotide matches and percent sequence identity when compared to the corresponding alignment generated by the preferred program.

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The invention is further to "functional variants" of the regulatory sequence disclosed. Functional variants include, for example, regulatory sequences of the invention having one or more nucleotide substitutions, deletions or insertions and wherein the variant retains promoter activity, particularly the ability to drive expression preferentially to the embryo of a plant. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of reporter activity as is described at U.S. Pat. No. 6,844,484, Northern blot analysis, or similar techniques. The '484 patent describes the identification of functional variants of different promoters.

The invention further encompasses a "functional fragment" that is a regulatory fragment formed by one or more deletions from a larger regulatory element. For example, the 5' portion of a promoter up to the TATA box near the transcription start site can be deleted without abolishing promoter activity, as described by Opsahl-Sorteberg, H-G. et al., 2004. Such fragments should retain promoter activity, particularly the ability to drive expression of operably linked nucleotide sequences. Activity can be measured by Northern blot analysis, reporter activity measurements when using transcriptional fusions, and the like. See for example, Sambrook et al. (1989). Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis et al. (1987) and Erlich, ed. (1989).

For example, a routine way to remove a part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at the 5' overhangs, blunt ends or nicks in the DNA template. However, the exonuclease III is unable to remove nucleotides at 3' 4-base overhangs. Timed digest of a clone with this enzyme produces unidirectional nested deletions.

The promoter of the invention may be combined with any number of other components to be introduced into the plant, including combined with a gene of interest to be expressed in the plant. The "gene of interest" refers to a nucleotide sequence that encodes for a desired polypeptide or protein but also may refer to nucleotide sequences that do not constitute an entire gene, and which do not necessarily encode a polypeptide or protein. For example, when used in a homologous recombination process, the promoter may be placed in a construct with a sequence that targets an area of the chromosome in the plant but may not encode a protein. If desired, the gene of interest can be optimized for plant translation by optimizing the codons used for plants and the sequence around the translational start site for plants. Sequences resulting in potential mRNA instability can also be avoided.

By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner. When referring to preferential expression, what is meant is expression at a higher level in the particular plant tissue than in other plant tissue. The present regulatory region confers expression preferentially in the embryo. When referring to an embryo preferred promoter is meant that it expresses an operably linked sequence to a higher degree in embryo tissue that in other plant tissue. It may express during embryo development, along with expression at other stages, may express strongly during embryo development and to a much lesser degree at other times.

The promoter of the invention may also be used in conjunction with another promoter. In one embodiment, the plant selection marker and the gene of interest can be both functionally linked to the same promoter. In another embodiment, the plant selection marker and the gene of interest can be functionally linked to different promoters. In yet third and fourth embodiments, the expression vector can contain two or more genes of interest that can be linked to the same promoter or different promoters. For example, the ZM embryo promoter PGNpr36 described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, the ubiquitin promoter (European patent application no. 0 342 926); the promoter for the small subunit of ribulose-1,5-bis-phosphate carboxylase (ssRUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten and Schell, 1985) that have plant activity; or viral promoters such as the cauliflower mosaic virus (CaMV) 19S and 35S promoters (Guilley et al., 1982; Odell et al., 1985), the figwort mosaic virus FLt promoter (Maiti et al., 1997) or the coat protein promoter of TMV (Grdzelishvili et al., 2000). Alternatively, plant promoters such as heat shock promoters for example soybean hsp 17.5-E (Gurley et al., 1986); or ethanol-inducible promoters (Caddick et al., 1998) may be used. See International Patent Application No. WO 91/19806 for a review of illustrative plant promoters suitably employed in the present invention.

A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements, which enable expression in the desired tissue such as the embryo can be identified, isolated, and used with other core promoters to confirm embryo-preferred expression. By core promoter is meant the sequence sometimes referred to as the TATA box (or similar sequence), which is common to promoters in most genes encoding proteins. Thus the upstream promoter of PGNpr36 can optionally be used in conjunction with its own or core promoters from other sources.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989).

One skilled in the art readily appreciates that the promoter can be used with any of a variety of nucleotide sequences comprising the gene of interest to be expressed in plants. For example, the gene of interest may encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. The sequences used with the promoter can be native or non-native sequences to the plant. DNA sequences native to plants as well as non-native DNA sequences can be transformed into plants and used to modulate levels of native or non-native proteins.

The gene of interest can also be a nucleotide sequence used to target an area of the plant genome through homologous recombination. The promoter may be placed in a construct with such sequence, which sequence will not necessarily encode a protein. The sequence recombines in the genome and the promoter may be placed at the desired site targeted by the sequences to regulate the desired endogenous nucleotide sequence.

Further, the promoter can be used to drive mRNA that can be used for a silencing system, such as antisense, and in that instance, no protein is produced. Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required.

Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene (such as the promoter of the invention or another promoter); and DNA elements that control the processing of transcripts, such as transcription termination/polyadenylation sequences. It also can contain such sequences as are needed for the eventual integration of the vector into the plant chromosome.

Clearly, many variations in use of the promoter of the invention are available to one skilled in the art.

In one embodiment, the expression vector also contains a gene encoding a selectable or scoreable marker that is operably or functionally linked to a promoter that controls transcription initiation, which can be the promoter of the invention or another promoter. By "operably linked" it is understood that the gene of interest (in this case the gene encoding a selectable or scoreable marker) is oriented in connection to the promoter such that the promoter initiates transcription of the gene in order to allow its expression of the resulting protein in plants. For a general description of plant expression vectors and reporter genes, see Gruber et al. (1993). In one embodiment, the selective gene is a glufosinate-resistance encoding DNA and in another embodiment it can be phosphinothricin acetyl transferase (pat) or a maize optimized pat gene under the control of the CaMV 35S promoter. Such pat genes confer resistance to the herbicide bialaphos (Gordon-Kamm et al., 1990).

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. One example of a plant signal sequence is the barley alpha-amylase secretion signal (Rogers, 1985). Many signal sequences are known in the art. See, for example Becker et al. (1992), Fontes et al. (1991), Matsuoka and Nakamura (1991), Gould et al. (1989), Creissen et al. (1992), Kalderon et al. (1984) and Stiefel et al. (1990).

Leader sequences can be included to enhance translation. Translation leaders are known in the art and include: picornavirus leaders, for example, EMCV leader (Encephalomyocarditis 5' noncoding region) (Elroy-Stein et al. (1989); potyvirus leaders, for example, TEV leader (Tobacco Etch Virus) (Gallie et al. (1995)); human immunoglobulin heavy-chain binding protein (BiP) (Macejak et al. (1991)); untranslated leader from the coat protein mRNA of alfalfa mosaic virus (AMV RNA 4) (Jobling et al. (1987)); tobacco mosaic virus leader (TMV) (Gallie. (1989)); and maize chlorotic mottle virus leader (MCMV) (Lommel et al. (1991)). See also, Della-Cioppa et al. (1987). Other methods known to enhance translation can also be utilized, for example, introns, and the like. Obviously, many variations on the promoters, selectable markers, signal sequences, leader sequences, termination sequences, introns, enhancers and other components of the construct are available to one skilled in the art.

Methods for introducing expression vectors into plant tissue available to one skilled in the art are varied and will depend on the plant selected. Procedures for transforming a wide variety of plant species are well known and described throughout the literature. See for example, Mild and McHugh (2004); Klein et al. (1992); and Weising et al. (1988). For example, the DNA construct may be introduced into the genomic DNA of the plant cell using techniques such as microprojectile-mediated delivery (Klein et al. 1992), electroporation (Fromm et al., 1985), polyethylene glycol (PEG) precipitation (Mathur and Koncz, 1998), direct gene transfer (WO 85/01856 and EP-A-275 069), in vitro protoplast transformation (U.S. Pat. No. 4,684,611), and microinjection of plant cell protoplasts or embryogenic callus (Crossway, 1985). Co-cultivation of plant tissue with *Agrobacterium tumefaciens* is another option, where the DNA constructs are placed into a binary vector system (Ishida et al., 1996). The virulence functions of the *Agrobacterium tumefaciens* host will direct the insertion of the construct into the plant cell DNA when the cell is infected by the bacteria. See, for example, Fraley et al. (1983).

Standard methods for transformation of canola are described by Moloney et al. (1989). Corn transformation is described by Fromm et al. (1990), and Gordon-Kamm et al. (1990). *Agrobacterium* is primarily used in dicots, but certain monocots such as maize can be transformed by *Agrobacterium*. See, for example, U.S. Pat. No. 5,550,318. Rice transformation is described by Hiei et al. (1994), and Lee et al. (1991). Wheat can be transformed by techniques similar to those used for transforming corn or rice. *Sorghum* transformation is described by Casas et al. (1993) and barley transformation is described by Wan and Lemaux (1994). Soybean transformation is described in a number of publications, including U.S. Pat. No. 5,015,580.

In one preferred method, the *Agrobacterium* transformation methods of Ishida et al. (1996) and also described in U.S. Pat. No. 5,591,616, are generally followed, with modifications that the inventors have found improve the number of transformants obtained. The Ishida method uses the A1188 variety of maize that produces Type I callus in culture. In one preferred embodiment the Hi II maize line is used which initiates Type II embryogenic callus in culture (Armstrong et al., 1991).

While Ishida recommends selection on phosphinothricin when using the bar or pat gene for selection, another preferred embodiment provides use of bialaphos instead. In general, as set forth in the U.S. Pat. No. 5,591,616, and as outlined in more detail below, dedifferentiation is obtained by culturing an explant of the plant on a dedifferentiation-inducing medium for not less than seven days, and the tissue during or after dedifferentiation is contacted with *Agrobacterium* having the gene of interest. The cultured tissue can be callus, an adventitious embryo-like tissue or suspension cells, for example. In this preferred embodiment, the suspension of *Agrobacterium* has a cell population of $10^6$ to $10^{11}$ cells/ml and are contacted for three to ten minutes with the tissue, or continuously cultured with *Agrobacterium* for not less than seven days. The *Agrobacterium* can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986).

Further, the Ishida protocol as described provides for growing fresh culture of the *Agrobacterium* on plates, scraping the bacteria from the plates, and resuspending in the co-culture medium as stated in the U.S. Pat. No. 5,591,616 for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase, and are harvested at a density of no more than $OD_{600=0.5}$, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985). The resuspension medium is the same as that described above. All further Hi II media are as described in Armstrong and Green (1985). The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

In accordance with the present invention, a transgenic plant is produced that contains an introduced PGNpr36. It can be combined with any one of the components set forth above. In a preferred embodiment, the promoter is driving expression of a nucleotide sequence such that the sequence encodes a protein preferentially expressed in the seed of the plant. Preferably, the plant is a cereal plant, and most preferably, a maize plant.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants, and selection for plants from subsequent generations which express the amino acid sequence. The plant breeding methods used herein are well known to one skilled in the art. For a discussion of plant breeding techniques, see Poehlman and Sleper (1995). Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in Brassica, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (Zea mays L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detas sling, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Neal (1988). In a typical backcross protocol, the original variety of interest (recurrent parent) is crossed to a second variety (non-recurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the non-recurrent parent.

EXAMPLES

The following is presented as illustrative of an embodiment of the invention and does not limit the scope of the invention as otherwise set forth.

Materials and Methods

Construction of cDNA Libraries Representative of Maize Embryo Tissues

Maize plants were grown from seed in moist soil under standard greenhouse conditions. Four lines of maize were grown, representative Lancaster, Stiff Stalk, high protein and high oil lines. Elite inbreds are commonly derived from germplasm pools known as Stiff Stalk and Lancaster. Stiff Stalk inbreds have been known for decades and are reported by the USDA to have been widely available for decades. They are derived from the Iowa Stiff Stalk synthetic population (Sprague, 1946). For example see PI accession no. 550481 and discussions of Stiff Stalk germplasm at U.S. Pat. Nos. 5,706,603; 6,252,148; 6,245,975; 6,344,599 and 5,134,074. See also, Neuhausen (1989). Lancaster inbreds are derived from the open pollinated variety Lancaster Surecrop (Anderson, 1944). See for example, PI 280061. High oil or high protein plants are those in which the oil or protein content of the seed is higher than lower oil or protein producing plants such as hybrid #2 yellow dent corn.

Plants were self-pollinated and individual plants were sacrificed at 10, 11, 12, 19, 28, 37 and 46 days post-pollination. Embryos were immediately harvested from these plants, frozen in liquid nitrogen and stored at −80° C. Embryos harvested from distinct lines and at different time points were kept separate, except that embryos of the same line harvested at 10, 11 and 12 days post-pollination were pooled. For each of the five resulting time points (10 to 12 days, 19 days, 28 days, 37 days and 46 days post-pollination) equal amounts of embryo tissues harvested from each of the four maize lines were pooled. Total RNA was isolated from the pooled embryo tissues using a phenol-based method (Chatterjee et al., 1996), and poly-A message was then prepared from this RNA using Poly(A) Quik mRNA isolation columns (Stratagene; La Jolla, Calif.). These poly-A RNA samples were used to prepare five cDNA libraries, each representative of all four maize lines and each corresponding to a different time point of embryo development. The libraries were constructed in the Lambda ZAP II vector (Stratagene; La Jolla, Calif.).

DNA Sequence Analysis of Representative Clones from Maize Embryo Libraries

For each of the five libraries, phagemids were excised from the phage vector. Approximately 100 clones were randomly selected to represent each library and the nucleotide sequences of the cDNA inserts were determined using the chain termination approach using attached dyes by the 'DNA Sequencing and Synthesis Facility' of Iowa State University (Ames, Iowa). Nucleotide sequences of clones were compared using the 'Sequencher' package (Gene Codes Corporation; Ann Arbor, Mich.).

Analysis of Clone Representation in a Developing Embryo Library by Plaque Hybridization Phage of an equal mixture of each of the five post-pollination embryo cDNA library time points was infected onto the bacterial strain XL1-Blue MRF' (Stratagene; La Jolla, Calif.) to generate approximately 80,000 plaques upon plating.

Phage DNA was transferred onto charged nylon filters (Amersham; Piscataway, N.J.) and cross-linked to the filters by exposure to ultraviolet light. Radionucleotide $^{32}$P) was incorporated into PGNpr36 cDNA sequence by random prime labeling (Feinberg and Vogelstein, 1983) using the 'High Prime' reagent mix (Roche Diagnostics GmbH; Mannheim, Germany) and the filters were incubated with this probe. Filters were washed under conditions of high stringency (15 mM NaCl, 1.5 mM sodium citrate [$Na_3C_6H_5O_7.2H_2O$], 0.1% sodium dodecyl sulfate, 65° C.) and exposed to BioMax MS film (Kodak; Rochester, N.Y.), to reveal clones homologous to PGNpr36 cDNA.

Analysis of Genome Organization by DNA Hybridization

DNA was prepared from maize leaves using a hexadecyl-trimethyl-ammonium bromide based method (Stacey and Issac, 1994). DNA (15 μg samples) was digested with the restriction endonucleases EcoRI or HindIII and DNA fragments were size separated on 0.7% agarose gels. Vector DNA was similarly digested and 60 pg was size separated on the gels. The DNA was transferred onto charged nylon filters (Amersham; Piscataway, N.J.) and cross-linked to the filters by exposure to ultraviolet light. Radionucleotide ($^{32}$P) was incorporated into PGNpr36 cDNA sequence by random prime labeling using the 'High Prime' reagent mix (Roche Diagnostics GmbH; Mannheim, Germany) and the filters were incubated with this probe. Filters were washed under conditions of high stringency (15 mM NaCl, 1.5 mM sodium citrate [$Na_3C_6H_5O_7.2H_2O$], 0.1% sodium dodecyl sulfate, 65° C.) and exposed to BioMax MS film (Kodak; Rochester, N.Y.).

Analysis of Message Levels by RNA Hybridization

Total RNA was isolated from maize tissues using a phenol-based method (Chatterjee et al., 1996). RNA (20 μg samples) was size separated on agarose/formaldehyde gels, transferred onto charged nylon filters (Amersham; Piscataway, N.J.) and cross-linked to the filters by exposure to ultraviolet light. Radionucleotide labeled DNA probes were prepared by random prime labeling using the 'High Prime' reagent mix (Roche Diagnostics GmbH; Mannheim, Germany) and the filters were incubated with maize PGNpr36 cDNA or 18S rRNA gene sequences. Filters were washed under conditions of high stringency (15 mM NaCl, 1.5 mM $Na_3C_6H_5O_7.2H_2O$, 0.1% sodium dodecyl sulfate, 65° C.) and exposed to BioMax MS film (Kodak; Rochester, N.Y.). DNA probes were stripped from filters by washing with near-boiling 0.1% sodium dodecyl sulfate.

Cloning of and Nucleotide Sequence Determination of a Maize pPGNpr36 Promoter

DNA sequences upstream of a PGNpr36 open reading frame were isolated from a maize Missouri-13 line genomic library in the Lambda FIX II vector (Stratagene; La Jolla, Calif.). The phage library was infected onto the bacterial strain XL1-Blue MRA (Stratagene; La Jolla, Calif.) and plated to generate plaques. Phage DNA was transferred onto charged nylon filters (Amersham; Piscataway, N.J.) and cross-linked to the filters by exposure to ultraviolet light. Radionucleotide ($^{32}$P) was incorporated into PGNpr36cDNA sequence by random prime labeling using the 'High Prime' reagent mix (Roche Diagnostics GmbH; Mannheim, Germany) and the filters were incubated with this probe. Filters were washed under conditions of high stringency (15 mM NaCl, 1.5 mM sodium citrate [$Na_3C_6H_5O_7.2H_2O$], 0.1% sodium dodecyl sulfate, 65° C.) and exposed to BioMax MS film (Kodak; Rochester, N.Y.) to reveal sequences homologous to the cDNA. Homologous clones were recovered and the phage inserts mapped by comparing restriction endonuclease digests of the clones following size fractionation via agarose gel electrophoresis. The nucleotide sequence of DNA identified as extending approximately 3 kb 5' of PGNpr36 open reading frame sequence was determined by the 'DNA Sequencing Facility' of Iowa State University (Ames, Iowa).

Construction of Promoter-Reporter Gene Fusions and Introduction into Plants

The here cloned approximately 3 kb of sequence 5' to the open reading frame, was fused to the β-glucoronidase (uidA) reporter gene of *Escherichia coli* (Jefferson et al., 1987). To ensure appropriate message termination, the potato proteinase inhibitor II (PinII) transcription terminator region was added 3' of the reporter genes for each fusion (An et al., 1989). These fusions were included on vectors that also carried the phosphinothricin N-acetyltransferase gene (pat) of *Streptomyces viridochromogenes* to confer herbicide resistance to transgenic plants. This gene confers resistance to bialaphos (Gordon-Kamm et al., 1990). The expression of the pat marker was controlled by the cauliflower mosaic virus 35S promoter and terminator sequences (Guilley et al., 1982; Odell et al., 1985). In addition, the vectors contained border sequences flanking the transcription units. These borders allowed the transformation of vector DNA enclosed within them into the target plant's genome. The vector is shown in FIG. 2.

The procedure for stable transformation was modified from that of Ishida et al. (1996) as described supra. Immature zygotic embryos from kernels of a Hi-II/elite line were transformed with *A. tumefaciens* strain EHA101 containing the relevant PGNpr36 upstream sequence/reporter fusions to generate transgenic events. $T_0$ plants were regenerated from tissue culture of each event, transferred to soil in a greenhouse and pollinated using pollen from an elite inbred line to produce $T_1$ seeds.

Quantification of uidA Reporter Gene Expression in Seed Tissues

Six dry seeds from each ear were individually pulverized and extracted with 1 ml of lysis buffer (50 mM sodium phosphate pH 7.0, 1 mM EDTA, 1 mM DTT). Furthermore, fifty seed pools from each ear were homogenized in a blender and three approximately 100 mg aliquots were extracted with the above lysis buffer. Single and pooled seed samples were placed in extraction tubes held in a rack, with a ball bearing added to each tube, and were then homogenized in a high-speed shaker for 20 seconds. Samples were centrifuged, and the supernatants recovered and stored on ice prior to analysis. Assays were performed in triplicate to determine GUS activity resulting from expression of the uidA reporter gene (Jefferson et al., 1987). Total soluble protein (1 μg) was incubated in 100 μl of lysis buffer and the reaction was initiated with 25 μl of 5 mM 4-methylumbelliferyl β-D-glucuronide (Sigma; St. Louis, Mo.). The reaction was incubated for up to 30 min at 37° C. At specific time points 25 μl volumes of the reaction mixture were transferred to PolySorp 96-well plates (Nalge Nunc International; Rochester, N.Y.) that had 175 μl of stop buffer (0.2M $Na_2CO_3$) per well. Fluorescence was measured at an excitation wavelength of 360 nm and an emission wavelength of 460 nm on a Microplate Fluorometer (Molecular Devices; Sunnyvale, Calif.). GUS protein levels were then calculated by comparison to a standard curve of 1 to 100 μM 4-methylumbelliferone (Sigma; St. Louis, Mo.). Protein concentrations were determined in duplicate using a dye-binding assay (Bradford, 1976).

The highest recorded expression level for an individual seed observed with regenerated plants that carried the construct was noted. This gives an indication of expression potential using the promoter sequence.

Analysis of uidA Reporter Gene Expression in Transgenic Plant Tissues $T_1$ seeds were sectioned using a scalpel and were incubated with Jefferson's buffer containing 0.5 mgml$^{-1}$ X-gluc (Jefferson et al., 1987) for up to 3 hours at 37° C. until a clear blue stain was visible. In addition, $T_1$ seeds were allowed to germinate and the resulting $T_1$ seedlings were self-pollinated or pollinated with pollen from the non-transgenic HiII maize line. Representative tissue samples were collected from selected non-seed tissues and were incubated overnight at 37° C. with Jefferson's buffer containing 0.5 mgml$^{-1}$ X-gluc (Jefferson et al., 1987). Blue staining indicated GUS activity. Furthermore, developing $T_2$ seeds were harvested at defined time points and were similarly treated to reveal GUS activity, with sufficient incubation times to reveal any clear staining.

Results

Identification of ZM Embryo PGNpr36 as Being Highly Expressed in the Developing Embryo The approach taken to identify promoters capable of driving foreign gene expression in maize embryo tissues was to examine relative levels of expression of native maize embryo genes. This was achieved by analyzing clone representation in cDNA libraries prepared from embryo tissues. To enable clones to be identified from various stages of seed development, libraries were prepared from embryo tissues harvested at five time points post-pollination. The selected time points were between 10 and 12 days post-pollination, and at 19, 28, 37 and 46 days post-pollination, the last time point corresponding to fully mature and dried seed. Furthermore, in order to identify clones that would be of value in different corn germplasms, each of the above five embryo pools was made up equally of embryos isolated from each of four lines of maize, comprising a Lancaster line, a Stiff Stalk line, a high protein line and a high oil line.

For each of the five embryo cDNA libraries the DNA sequence of approximately one hundred randomly selected clones was determined. The approximately five hundred cDNA sequences that were so generated were analyzed to reveal the gene expression profile of developing maize embryos and to identify the most highly represented sequences. These sequences were considered to correspond to the most abundant clones or families of clones in the libraries and therefore to the most highly expressed genes or families of genes.

Using this approach PGNpr36 was identified as being one of the most highly expressed sequences, with a total of four hits out of 530 cloned sequences. This indicates that approximately 0.8% of mRNA molecules present in developing maize embryo tissues encode PGNpr36. However, the representation of PGNpr36 message varies throughout embryo development. No PGNpr36 sequences were identified among approximately one hundred randomly selected clones from the 10 to 12-day post-pollination cDNA library. By contrast, one and three PGNpr36 sequences were identified among a similar number of clones selected from the 28 and 37-day post-pollination cDNA libraries, respectively. Thus, expression of PGNpr36 appears to increase later during embryo development, peaking at about 37 days post-pollination.

Confirmation of PGNpr36 as Being Highly Expressed in the Developing Maize Embryo Sequence encoding PNGpr36 was then confirmed as being highly expressed with a greater level of confidence. A region of the PGNpr36 clone was screened for hybridization against a random plating of approximately 80,000 plaques of an equally represented mixture of the five post-pollination embryo cDNA library time points. Thus, a representative pool of plaques corresponding to all four lines of maize and all five time points was assessed. Sequence of a strongly expressed gene should identify a relatively high proportion of plaques, comparable to its representation in the cDNA libraries. Since tens of thousands of plaques were screened there is a greater confidence that the result is representative of all sequences, compared to results obtained using the more restricted DNA sequencing approach described above to initially identify highly expressed clones. This plaque hybridization approach identified approximately 0.6% of the cDNA clones as being PNGpr36.

This is consistent with one or at most a few PGNpr36 or PGNpr36 like sequences being present in the maize genome. Thus, the estimation of PGNpr36 clone representation using plaque hybridization data should not be greatly distorted by gene copy number considerations, particularly since some sequences identified by the copy number determination approach may represent pseudogenes that produce no transcripts. In the seed PNGpr36 message is predominantly located in developing embryo tissues The tissue and line specificity of expression for PGNpr36 was then assessed at the messenger RNA level by conducting a hybridization analysis using PGNpr36 cDNA sequence as a probe and RNA prepared from various tissues as the templates For non-seed material the tissues providing the RNA were pooled samples collected from the four maize lines originally used to make the cDNA libraries. Expression was assessed in leaf, stem, root, tassel, anther, pollen, husk, silk, immature ear and cob tissues. However, in the case of seed tissues expression was assessed in 28-day post-pollination embryos isolated separately from each of the four maize lines used to make the cDNA libraries and in 28-day post-pollination embryos and endosperm tissues isolated from a standard maize laboratory line. In providing initial assessment, strong signals were observed with RNA prepared from embryos of each line, and only very weak signal in Missouri-13 endosperm tissue with the PGNpr36 sequences.

Expression was analyzed with RNA hybridization analysis using RNA from the tissues pooled from the maize lines. RNA hybridizing to PGNpr36 sequence was detected in 28-day post-pollination embryo tissue of all four maize lines used to make the cDNA libraries and of the standard laboratory line. By contrast, PGNpr36 message was not detected in endosperm tissue of the standard laboratory line, indicating that within the seed PNGpr36 much more highly expressed in the embryo than the endosperm. No PGNpr36 message was detected in stem, leaf, root, tassel, anther, pollen, husk, silk, immature ear or cob tissues. Thus, there is a strong seed preference for the expression of PGNpr36.

Novel Sequences are Located within the Approximately 3 kb of Sequence 5' and Proximal to the PGNpr36 Open Reading Frame Since expression of PNGpr36 was demonstrated to be predominantly in embryo tissue, and it was identified by the library sampling approach deployed here, an extensive genomic clone spanning approximately 2990 bases of the proximal promoter sequence and leader sequence of a gene, was isolated. These sequences were cloned from a library of genomic sequences prepared from leaf tissue of a standard maize laboratory line, using cDNA sequence as a probe. Plaques were thus identified in the genomic library as carrying homologous sequences to Genomic DNA extending approximately 3 kb upstream of the translation start codon for this gene was sub-cloned and the nucleotide sequence determined See FIG. 1 showing the promoter with ATG site underlined (SEQ ID NO: 2). The promoter is SEQ ID NO: 1.

The sequence shows no significant identity to more than 35-227 nucleotide bases of any other sequence. The here cloned genomic sequence shows a region of similarity to small regions of large sequence in the Genbank/EMBL databases. For example, GenBank Acc. No. AC214353.4 is a *Zea mays* BAC clone, CR201-188G11 from chromosome 5 and GenBank Acc. No. BT038630.1, a *Zea mays* full length cDNA clone ZM_BFb0298119 mRNA, both with a less than 230 base region of 85% identity. The sequence shows 95% identity over 108 bases of two *Zea mays* clones, GenBank Acc. Nos. EU941551.1 and EU940752.1; 94% identity to less than 100 bases of *Zea mays* cDNA GenBank Acc. No. BT084022.1 and NCBI Ref. No. NM_001154561.1; 93% identity to less than 62 bases of *Zea mays* clones NCBI Ref. Nos. NM_001152370.1, NM_001147188.1 and 92% identity to a *Zea mays* clone GenBank BT024168.1 and 97% identity to 35 bases of a *Zea mays* clone GenBank Acc. No. EU97488.1.

The PGNpr36 Promoter Sequence can Drive Transgene Expression in Stably Transformed Seed Tissue To assess the activity and specificity of the PGNpr36 promoter sequence a transcription unit was made in which the PGNpr36 sequence was fused to DNA encoding the uidA reporter gene. The potato protease inhibitor II (PinII) terminator sequence was positioned downstream of the uidA coding sequence. This transcription unit was included in a plant transformation vector. The resulting construct is shown in FIG. 2.

The promoter-reporter fusion was then stably introduced into the maize genome by *Agrobacterium* mediated transformation. Following the transformation of developing embryo tissues, uidA expression was assessed in non-differentiated callus tissue prior to plant regeneration. GUS activity was detected in callus tissue derived from transformation experiments using the promoter-reporter fusion.

Plants were then regenerated from transformation events obtained using the vector. A total of 194 plants were regenerated from 22 independent transformation events obtained using the PGNpr36 promoter-uidA fusion with several plants from each event. Seed was harvested, the soluble protein was extracted, and for each plant the level of GUS was determined in each of six randomly selected seeds and also on a pool of 50 randomly selected seeds.

Figure 3:
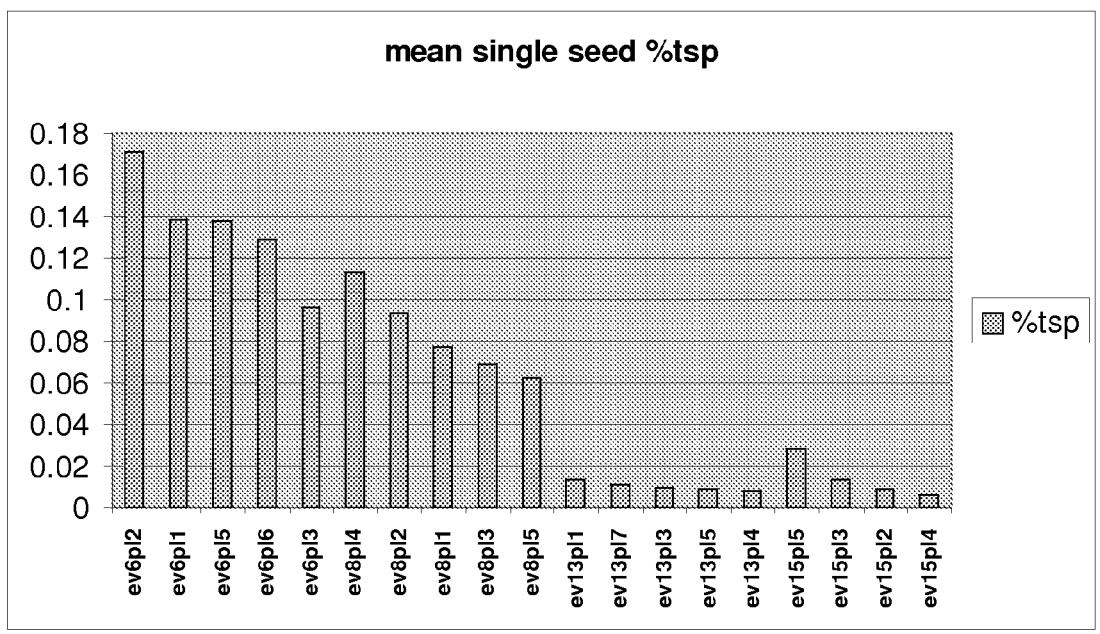
FIG. 3 is a graph summarizing recombinant protein level data derived from single seed analysis of transgenic maize carrying the PGNpr36 ZM embryo promoter. There are four different events represented with one to four plants analyzed for each event. The cut off value for detecting expression is 0.006% of total soluble protein (TSP), and non-transgenic control lines never approach this level.

The GUS levels for the transgenic seed are summarized in graphically in FIG. 3. The mean GUS level achieved using the PGNpr36 promoter was calculated in several alternative ways. Alternative methods of analysis were based on all seeds that had detectable levels of GUS for each plant or only on the seed that had the highest level of GUS for each plant. Also, the mean GUS expression level obtained using the construct was based either on mean expression levels for each independent transformation event, or for each transgenic plant, or on data for each seed. Negative GUS expression data was not included in the analysis. Furthermore, the calculations were either based on individual seed data or on bulk seed data where protein was extracted from a pool of 50 seed. In any bulk sample approximately half the seed are anticipated to be nulls, so that GUS levels calculated from bulk seed analyses are expected to be less than those calculated from single seed analyses. FIG. 3 shows single seed assay for plants from four different events and is also summarized in the table below.

TABLE 1

| plant (event no./plant no.) | % Total Soluble Protein |
|---|---|
| ev1pl1 | 0.077 |
| ev1pl2 | 0.033 |
| ev1pl3 | 0.100 |

TABLE 1-continued

| plant (event no./plant no.) | % Total Soluble Protein |
|---|---|
| ev1pl4 | 0.060 |
| ev2pl1 | 0.065 |
| ev2pl2 | 0.037 |
| ev2pl3 | 0.065 |
| ev2pl4 | 0.063 |
| ev3pl4 | 0.04 |
| ev4pl1 | 0.043 |
| ev4pl2 | 0.042 |
| ev4pl3 | 0.031 |
| ev5pl1 | 0.045 |
| ev5pl2 | 0.055 |
| ev5pl3 | 0.093 |
| ev5pl4 | 0.062 |
| ev6pl2 | 0.171 |
| ev6pl1 | 0.138 |
| ev6pl5 | 0.138 |
| ev6pl6 | 0.129 |
| ev6pl3 | 0.096 |
| ev8pl4 | 0.113 |
| ev8pl2 | 0.093 |
| ev8pl1 | 0.077 |
| ev8pl3 | 0.069 |
| ev8pl5 | 0.062 |
| ev9pl1 | 0.157 |
| ev9pl2 | 0.148 |
| ev9pl3 | 0.176 |
| ev9pl4 | 0.144 |
| ev10pl2 | 0.017 |
| ev10pl3 | 0.015 |
| ev10pl7 | 0.019 |
| ev10pl9 | 0.029 |
| ev13pl1 | 0.013 |
| ev13pl7 | 0.011 |
| ev13pl3 | 0.01 |
| ev13pl5 | 0.009 |
| ev13pl4 | 0.008 |
| ev15pl5 | 0.028 |
| ev15pl3 | 0.013 |
| ev15pl2 | 0.009 |
| ev15pl4 | 0.006 |

Figure 4:
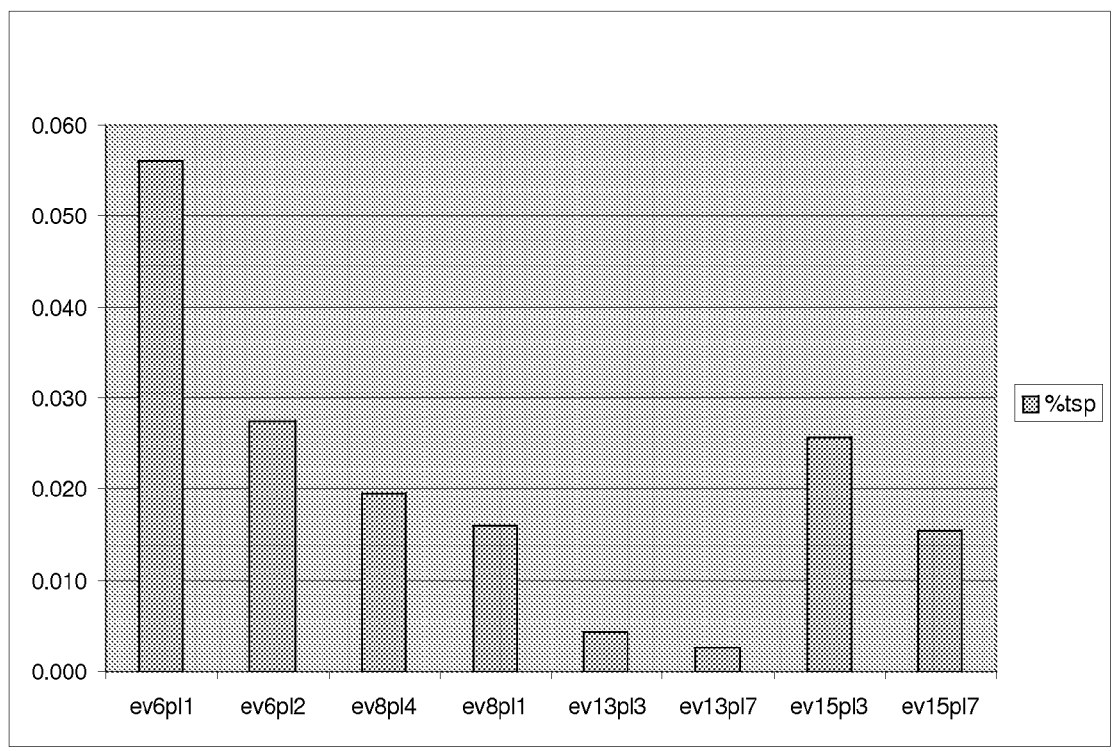
FIG. 4 is a graph summarizing recombinant protein level data for pooled seed of individual transgenic maize plants carrying the PGNpr36 ZM embryo promoter. The cut off value for detecting expression is 0.006% of total soluble protein (TSP), and non-transgenic control lines never approach this level.

FIG. 4 shows activity in pooled seed for individual plants and reflected in the table below.

TABLE 2

| sample | % tsp |
|---|---|
| ev6pl1 | 0.056 |
| ev6pl2 | 0.027 |
| ev8pl4 | 0.020 |
| ev8pl1 | 0.016 |
| ev15pl3 | 0.026 |
| ev15pl7 | 0.015 |

The PGNpr36 promoter sequence can clearly drive reporter gene expression in seed. Depending on the method of analysis, mean GUS levels for single T₁ seed vary from 0.006% to 0.176% of total soluble protein, whereas mean GUS levels for bulk T₁ seed vary from up to 0.056% of total soluble protein. Also, as a guide to the potential of the PGNpr36 promoter sequence to facilitate protein production in plants, the highest level of GUS recorded in a single seed was noted. This highest recorded level of GUS was 0.454% of total soluble protein for a single seed.

The tissue specificity of expression using the PGNpr36 promoter was then assessed. Three of the highest expressing lines for the construct, each from a separate transformation event, were grown in the next generation from T₁ seeds and were assessed in a wide range of non-seed tissues. Representative tissue samples were collected from leaves at 21 days post-germination and at 12 days post-pollination. Stem, root and silk tissues were also collected at 12 days post-pollination, and husk and cob tissues at 19 days post-pollination. All tissue samples were treated to reveal any evidence of GUS activity. The PGNpr36 promoter showed no indication of driving GUS activity in any of the above tissues, with the exception of the pericarp, and the cob tissue, which showed faint localized non-uniform staining. Thus, apart from in cob tissue, the promoter sequence does not drive expression in non-seed tissues, and even in the cob expression is weak. Expression of the uidA reporter gene was also assessed in $T_1$ seed tissues harvested directly from the $T_0$ transgenic plants. Fully mature dried down seeds were sliced in half and treated to reveal GUS activity. Strong blue staining was observed in the embryo, but no staining was observed in endosperm or aleurone/pericarp tissues. Thus, within the seed, expression appears to be localized to the embryo.

The specificity of PGNpr36 promoter was also assessed in seed tissues throughout development. The same plants were utilized as those used to examine non-seed tissue expression, described above. Three of the highest expressing lines, each from a separate transformation event, were grown from $T_1$ seeds. Seed tissues were collected at 12, 19, 27 or 28 and 36 or 37 days post-pollination, the final point corresponding approximately to seed maturity. Seed was then treated to reveal GUS activity. Also, seed tissues were assessed following a dry down period of approximately three weeks. For the 27/28 and 36/37-day post-pollination material and for the dried down material, the seeds were sliced in half prior to the treatment in order to more clearly reveal the pattern of embryo, endosperm and aleurone/pericarp expression. However, for 12 and 19-day post-pollination material, tissue specificity was determined by dissecting out the embryo from the surrounding endosperm prior to the treatment of each tissue type and in instances where embryos could not be removed, cutting the seed in half. The tissue was stained in the same tube. The staining pattern indicating GUS activity in seed tissues throughout development is summarized in Table 3.

TABLE 3

Tissue specificity of the globulin-2 promoter -uidA reporter fusions in developing $T_2$ seeds.

| Tissue[a] | GUS staining |
|---|---|
| 12-day embryo | Localized[b] |
| 12-day endosperm | Negative |
| 12-day aleurone/pericarp | Localized |
| 19-day embryo | Localized |
| 19-day endosperm | Faint |
| 19-day aleurone/pericarp | localized |
| ~28-day embryo | Localized |
| ~28-day endosperm | Faint |
| ~28-day aleurone/pericarp | Localized |

[a]The time points are relative to pollination and the final samples were assessed after approximately 3 weeks dry down.
[b]Two of the three lines examined showed staining.

GUS activity is evident in embryo tissues 12 days after pollination with two of the three lines tested. At this stage of development no staining is evident in the endosperm. The 19-day post-pollination developing seeds are much larger than the 12-day seeds, and the embryos stained for both lines tested. At this stage some staining is observed in the aleurone/pericarp as well as some very faint expression in the endosperm. By 27/28 days post-pollination the developing seeds have further enlarged, and GUS activity within the embryo is particularly evident in the scutellum. Also, some diffuse, faint GUS activity is evident in the endosperm at 27/28 days post-pollination, although the degree of staining is much fainter in the endosperm than in the embryo. Some GUS activity was again observed at this stage in surrounding aleurone/pericarp tissue. Overall, in developing seed tissues GUS activity is strongly embryo preferred, with the scutellum being the site of strongest activity within the embryo. Expression is becoming evident at 12 days post-pollination, and GUS staining is clear right through to the dried down seed stage.

The above experiments confirmed PGNpr36 message as being prevalent messages in maize embryos by sampling cDNA libraries representing embryo tissues from diverse lines at different stages of development. From a genomic clone extending upstream of the maize PGNpr36 translation start codon, approximately 3 kb of PGNpr36 promoter sequence was isolated and the nucleotide sequence determined. When fused to the uidA reporter gene and transformed back into maize, this promoter sequence could clearly drive reporter gene activity.

The PGNpr36 promoter cloned here appears to have a high tissue specificity, with reporter gene expression being seed specific apart from some possible minor activity in the cob, though even this possibly represents an overflow from seed activity. The PGNpr36 promoter can drive embryo expression as early as 12 days after pollination and appears increased by 28 days after pollination, and activity continues throughout embryo development, though with uidA as the reporter gene the presence of GUS activity in late stage embryos may reflect upon previously synthesized protein rather than active transcription and translation. The expression profile observed using the uidA reporter is in line with the observed abundance of cDNAs in the developmental seed libraries, where the native full length PGNpr36 promoter appears not to be as active in young developing embryo tissue as in maturing tissue, particularly 28-day post-pollination tissue. During the later stages of seed development promoter activity within the embryo is strongest in the scutellum. Some expression is also observed in the aleurone/pericarp.

The strong highly embryo preferred activity of the here cloned maize PGNpr36 promoter makes it an excellent choice for seed preferred/specific expression in plants, preferably maize, and other cereals.

REFERENCES

Altschul, S. F., Gish, W., Miller, W., Myers, E. W. and Lipman, D. J. (1990) Basic local alignment search tool. J. Mol. Biol. 215, 403-410.

Altschul, S. F., Madden, T. L., Schaffer, A. A., Zhang, J., Zhang, Z., Miller, W. and Lipman, D. J. (1997) Nucleic Acids Res. 25, 3389-3402.

An, G., Mitra, A., Choi, H. K., Costa, M. A., An, K., Thornburg, R. W. and Ryan, C. A. (1989) Functional analysis of the 3' control region of the potato wound-inducible proteinase inhibitor II gene. Plant Cell 1, 115-122.

Anderson, E. (1944) Sources of effective germplasm in hybrid maize. Annals of the Missouri Botanical Garden 31, 355-361.

Armstrong, C. I. and Green, C. E. (1985) Establishment and maintenance of friable, embryogenic maize callus and involvement of L-proline. Planta 154, 207-214.

Armstrong, C., Green, C. and Phillips, R. (1991) Development and availability of germplasm with high type II culture response. Maize Genet. Coop. News Lett. 65, 92-93.

Ausubel F. M., Brent, R., Kingston, R. E., Moore, D. D., Seidman, J. G., Smith, J. A. and Struhl, K. (Eds.) (1993) Current Protocols in Molecular Biology, John Wiley & Sons, New York.

Bailey, M. R., Woodard, S. L., Callaway, E., Beifuss, K., Magallanes-Lundback, M., Lane, J. R., Horn, M. E., Mallubhotla, H., Delaney, D. D., Ward, M., Van Gastel, F., Howard, J. A. and Hood, E. E. (2004) Improved recovery of active recombinant laccase from maize seed. Appl. Microbiol. Biotechnol. 63, 390-397.

Becker, T. W., Templeman, T. S., Viret, J. F. and Bogorad, L. (1992) The cab-m7 gene: a light-inducible, mesophyll-specific gene of maize. Plant Mol. Biol. 20, 49-60.

Belanger, F. C. and Kriz, A. L. (1991) Molecular basis for allelic polymorphism of the maize globulin-1 gene. Genetics 129, 863-872.

Bradford, M. M. (1976) A rapid and sensitive method for the quantitation of microgram quantities of protein utilizing the principle of protein-dye binding. Anal. Biochem. 72, 248-254.

Brinch-Pedersen, H., Hatzack, F., Sorensen, L. D. and Holm, P. B. (2003) Concerted action of endogenous and heterologous phytase on phytic acid degradation in seed of transgenic wheat (*Triticum aestivum* L.). Transgenic Res. 12, 649-659.

Broglie, R., Coruzzi, G., Fraley, R. T., Rogers, S. G., Horsch, R. B., Niedermeyer, J. G., Fink, C. L. and Chua, N. H. (1984) Light-regulated expression of a pea ribulose-1,5-bisphosphate carboxylase small subunit gene in transformed plant cells. Science 224, 838-843.

Bustos, M. M., Guiltinan, M. J., Jordano, J., Begum, D., Kalkan, F. A. and Hall, T. C. (1989) Regulation of beta-glucuronidase expression in transgenic tobacco plants by an A/T-rich, cis-acting sequence found upstream of a French bean beta-phaseolin gene. Plant Cell 1, 839-853.

Caddick M. X., Greenland, A. J., Jepson, I., Krause, K. P., Qu, N., Riddell, K. V., Salter, M. G., Schuch, W., Sonnewald, U. and Tomsett, A. B. (1998) An ethanol inducible gene switch for plants used to manipulate carbon metabolism. Nat. Biotechnol. 16, 177-180.

Carrillo, C., Wigdorovitz, A., Oliveros, J. C., Zamorano, P. I., Sadir, A. M., Gomez, N., Salinas, J., Escribano, J. M. and Borca, M. V. (1998) Protective immune response to foot-and-mouth disease virus with VP1 expressed in transgenic plants. J. Virol. 72, 1688-1690.

Casas, A. M., Kononowicz, A. K., Zehr, U. B., Tomes, D. T., Axtell, J. D., Butler, L. G., Bressan, R. A. and Hasegawa P. M. (1993) Transgenic sorghum plants via microprojectile bombardment. Proc. Natl. Acad. Sci. USA 90, 11212-11216.

Chatterjee, M., Sparvoli, S., Edmunds, C., Garosi, P., Findlay, K. and Martin, C. (1996) DAG, a gene required for chloroplast differentiation and palisade development in *Antirrhinum majus*. EMBO J. 15, 4194-4207.

Christensen, A. H., Sharrock, R. A. and Quail, P. H. (1992) Maize polyubiquitin genes: structure, thermal perturbation of expression and transcript splicing, and promoter activity following transfer to protoplasts by electroporation. Plant Mol. Biol. 18, 675-689.

Cornejo, M. J., Luth, D., Blankenship, K. M., Anderson, O. D. and Blechl, A. E. (1993) Activity of a maize ubiquitin promoter in transgenic rice. Plant Mol. Biol. 23, 567-581.

Corpet, F. (1988) Multiple sequence alignment with hierarchical clustering. Nucleic Acids Res. 16, 10881-10890.

Coruzzi, G., Broglie, R., Edwards, C. and Chua, N. H. (1984) Tissue-specific and light-regulated expression of a pea nuclear gene encoding the small subunit of ribulose-1,5-bisphosphate carboxylase. EMBO J. 3, 1671-1679.

Creissen, G., Edwards, E. A., Enard, C., Wellburn, A. and Mullineaux, P. (1992) Molecular characterization of glutathione reductase cDNA from pea (*Pisum sativum* L.). Plant J. 2, 129-131.

Crossway, A. (1985) Mol. Gen. Genet. 202, 179-185.

Daniell, H., Streatfield, S. J. and Wycoff, K. (2001) Medical molecular farming: production of antibodies, biopharmaceuticals and edible vaccines in plants. Trends Plant Sci. 6, 219-226.

De Wilde, C., Van Houdt, H., De Buck, S., Angenon, G., De Jaeger, G. and Depicker, A. (2000) Plants as bioreactors for protein production: avoiding the problem of transgene silencing. Plant Mol. Biol. 43, 347-359.

Erlich, ed. (1989) PCR Technology (Stockton Press, New York).

Feinberg, A. P. and Vogelstein, B. (1983) A technique for radiolabeling DNA restriction endonuclease fragments to high specific activity. Anal. Biochem. 132, 6-13.

Fontes, E. B., Shank, B. B., Wrobel, R. L., Moose, S. P., OBrian, G. R., Wurtzel, E. T. and Boston, R. S. (1991) Characterization of an immunoglobulin binding protein homolog in the maize floury-2 endosperm mutant. Plant Cell 3, 483-496.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L. and Woo, S. C. (1983) Expression of bacterial genes in plant cells. Proc. Natl. Acad. Sci. USA, 80, 4803-4807.

Fromm, M., Taylor, L. P. and Walbot, V. (1985) Expression of genes transferred into monocot and dicot plant cells by electroporation. Proc. Natl. Acad. Sci, USA 82, 5824-5828.

Fromm, M. E., Morrish, F., Armstrong, C., Williams, R., Thomas, J. and Klein, T. M. (1990) Inheritance and expression of chimeric genes in the progeny of transgenic maize plants. Biotechnology (N Y) 8, 833-839.

Geffers, R., Cerff, R. and Hehl, R. (2000) Anaerobiosis-specific interaction of tobacco nuclear factors with cis-regulatory sequences in the maize GapC4 promoter. Plant Mol. Biol. 43, 11-21.

Gordon-Kamm, W., Dilkes, B. P., Lowe, K., Hoerster, G., Sun, X., Ross, M., Church, L., Bunde, C., Farrell, J., Hill, P., Maddock, S., Snyder, J., Sykes, L., Li, Z., Woo, Y. M., Bidney, D. and Larkins, B. A. (1990) Transformation of maize cells and regeneration of fertile transgenic plants. Plant Cell 2, 603-618.

Gould, S. J., Keller, G. A., Hosken, N., Wilkinson, J. and Subramani, S. (1989) A conserved tripeptide sorts proteins to peroxisomes. J. Cell. Biol. 108, 1657-1664.

Grdzelishvili, V. Z., Chapman, S. N., Dawson, W. O. and Lewandowski, D. J. (2000) Mapping of the tobacco mosaic virus movement protein and coat protein subgenomic RNA promoters in vivo. Virology 275, 177-192.

Gruber et al. (1993) Vectors for plant transformation. In: Glick, B. R. and Thompson J. E. (Eds.) Methods in Plant Molecular Biology and Biotechnology, CRC Press, pp. 89-119.

Guilley, H., Dudley, R. K., Jonard, G., Balazs, E. and Richards, K. E. (1982) Transcription of Cauliflower mosaic virus DNA: detection of promoter sequences, and characterization of transcripts. Cell 30, 763-773.

Gurley, W. B., Czarnecka, E., Nagao, R. T. and Key, J. L. (1986) Upstream sequences required for efficient expression of a soybean heat shock gene. Mol. Cell. Biol. 6, 559-565.

Haq, T. A., Mason, H. S., Clements, J. D. and Arntzen, C. J. (1995) Oral immunization with a recombinant bacterial antigen produced in transgenic plants. Science 268, 714-716.

Hiei, Y., Ohta, S., Komari, T. and Kumashiro, T. (1994) Efficient transformation of rice (Oryza sativs L.) mediated by Agrobacterium and sequence analysis of the boundaries of the T-DNA. Plant J. 6, 271-282.

Higgins, D. G. and Sharp, P. M. (1988) CLUSTAL: a package for performing multiple sequence alignment on a microcomputer. Gene 73, 237-244.

Higgins, D. G. and Sharp, P. M. (1989) Fast and sensitive multiple sequence alignments on a microcomputer. Comput. Appl. Biosci. 5, 151-153.

Hood, E. E., Helmer, G. L., Fraley, R. T. and Chilton, M. D. (1986) The hypervirulence of Agrobacterium tumefaciens A281 is encoded in a region of pTiBo542 outside of T-DNA. J. Bacteriol. 168, 1291-1301.

Hood, E. E., Witcher, D. R., Maddock, S., Meyer, T., Baszczynski, C., Bailey, M., Flynn, P., Register, J., Marshall, L., Bond, D., Kulisek, E., Kusnadi, A., Evangelista, R., Nikolov, Z., Wooge, C., Mehigh, R. J., Hernan, R., Kappel, W. K., Ritland, D., Li, C-P. and Howard, J. A. (1997) Commercial production of avidin from transgenic maize: characterization of transformant, production, processing, extraction and purification. Mol. Breed. 3, 291-306.

Hood, E. E., Woodard, S. L. and Horn, M. E. (2002) Monoclonal antibody manufacturing in transgenic plants—myths and realities. Cum Opin. Biotechnol. 13, 630-635.

Hood, E. E., Bailey, M. R., Beifuss, K., Magallanes-Lundback, M., Horn, M. E., Callaway, E., Drees, C., Delaney, D. E., Clough, R. and Howard, J. A. (2003) Criteria for high-level expression of a fungal laccase gene in transgenic maize. Plant Biotechnol. J. 1, 129-140.

Huang, X., Miller, W., Schwartz, S. and Hardison, R. C. (1992) Parallelization of a local similarity algorithm. Comput. Appl. Biosci. 8, 155-65.

Innis, M., Gelfand, D., Sninsky, J. and White, T. (1990) PCR Protocols: A Guide to Methods and Applications. Academic Press, New York.

Innis, M., Gelfand, D. and Sninsky, J. (1995) PCR Strategies. Academic Press, New York.

Innis, M., Gelfand, D. and Sninsky, J. (1999) PCR Applications: Protocols for Functional Genomics. Academic Press, New York.

Ishida, Y., Saito, H., Ohta, S., Hiei, Y., Komari, T. and Kumashiro, T. (1996) High efficiency transformation of maize (Zea mays L.) mediated by Agrobacterium tumefaciens. Nat. Biotechnol. 14, 745-750.

Jefferson, R. A., Kavanagh, T. A. and Bevan, M. W. (1987) GUS fusions: beta-glucuronidase as a sensitive and versatile gene fusion marker in higher plants. EMBO J. 6, 3901-7.

Kalderon, D., Roberts, B. L., Richardson, W. D. and Smith A. E. (1984) A short amino acid sequence able to specify nuclear location. Cell 39, 499-509.

Karlin, S. and Altschul, S. F. (1990) Methods for assessing the statistical significance of molecular sequence features by using general scoring schemes. Proc. Natl. Acad. Sci. USA 87, 2264-2268.

Karlin, S. and Altschul, S. F. (1993) Applications and statistics for multiple high-scoring segments in molecular sequences. Proc. Natl. Acad. Sci. USA 90, 5873-5877.

Klein, T. M., Arentzen, R., Lewis, P. A. and Fitzpatrick-McElligott, S. (1992) Transformation of microbes, plants and animals by particle bombardment. Biotechnology (N Y) 10, 286-291.

Lamphear, B. J., Streatfield, S. J., Jilka, J. M., Brooks, C. A., Barker, D. K., Turner, D. D., Delaney, D. E., Garcia, M., Wiggins, W., Woodard, S. L., Hood, E. E., Tizard, I. R., Lawhorn, B. and Howard, J. A. (2002) Delivery of subunit vaccines in maize seed. J. Control. Release 85, 169-180.

Lee, N., Wang, Y., Yang, J., Ge, K., Huang, S., Tan, J. and Testa, D. (1991) Efficient transformation and regeneration of rice small cell groups. Proc. Nat. Acad. Sci. USA 88, 6389-6393.

Lessard, P. A., Kulaveerasingam, H., York, G. M., Strong, A. and Sinskey, A. J. (2002) Manipulating gene expression for the metabolic engineering of plants. Metab. Eng. 4, 67-79.

Leung, J., Fukuda, H., Wing, D., Schell, J. and Masterson, R. (1991) Functional analysis of cis-elements, auxin response and early developmental profiles of the mannopine synthase bi-directional promoter. Mol. Gen. Genet. 230, 463-474.

Maiti, I. B., Gowda, S., Kiernan, J., Ghosh, S. K. and Shepherd, R. J. (1997) Promoter/leader deletion analysis and plant expression vectors with the figwort mosaic virus (FMV) full length transcript (FLt) promoter containing single or double enhancer domains. Transgenic Res. 6, 143-156.

Mason, H. S., Lam, D. M. and Arntzen, C. J. (1992) Expression of hepatitis B surface antigen in transgenic plants. Proc. Natl. Acad. Sci. USA 89, 11745-11749.

Mathur, J. and Koncz, C. (1998) PEG-mediated protoplast transformation with naked DNA. Methods Mol. Biol. 82, 267-276.

Matsuoka, K. and Nakamura, K. (1991) Propeptide of a precursor to a plant vacuolar protein required for vacuolar targeting. Proc. Natl. Acad. Sci. USA 88, 834-838.

Meinkoth, J. and Wahl, G. (1984) Hybridization of nucleic acids immobilized on solid supports. Anal. Biochem. 138, 267-284.

Miki, B. and McHugh, S. (2004) Selectable marker genes in transgenic plants: applications, alternatives and biosafety. J. Biotechnol. 107, 193-232.

Moloney, M. et al. (1989) High efficiency transformation of Brassica napus using Agrobacterium vectors. Plant Cell Reports 8, 238-242.

Mullis et al. (1987) Methods Enzymol. 155:335-350 Myers, E. W. and Miller, W. (1988) Optimal alignments in linear space. Comput. Appl. Biosci. 4, 11-17.

Needleman, S. B. and Wunsch, C. D. (1970) A general method applicable to the search for similarities in the amino acid sequence of two proteins. J. Mol. Biol. 48, 443-453.

Nessler, C. L. (1994) Metabolic engineering of plant secondary products. Transgenic Res. 3, 109-115.

Neuhausen, S. (1989) A survey of Iowa Stiff Stalk parents derived inbreds and BSSS(HT)C5 using RFLP analysis. MNL 63, 110-111.

Odell, J. T., Nagy, F. and Chua, N. H. (1985) Identification of DNA sequences required for activity of the cauliflower mosaic virus 35S promoter. Nature 313, 810-812.

Oldach, K. H., Becker, D. and Lorz, H. (2001) Heterologous expression of genes mediating enhanced fungal resistance in transgenic wheat. Mol. Plant. Microbe Interact. 14, 832-838.

Pearson, W. R. and Lipman, D. J. (1988) Improved tools for biological sequence comparison. Proc. Natl. Acad. Sci. USA 85, 2444-2448.

Pearson, W. R. (1994) Using the FASTA program to search protein and DNA sequence databases. Methods Mol. Biol. 24, 307-331.

Poehlman, J. M. and Sleper, D. A. (1995) Breeding field crops, 4th Edition, Iowa State University Press.

Poirier, Y., Nawrath, C. and Somerville, C. (1995) Production of polyhydroxyalkanoates, a family of biodegradable plastics and elastomers, in bacteria and plants. Biotechnology (N Y) 13, 142-150.

Rogers, J. C. (1985) Two barley alpha-amylase gene families are regulated differently in aleurone cells. J. Biol. Chem. 260, 3731-3738.

Roussell, D. L., Boston, R. S., Goldsbrough, P. B. and Larkins, B. A. (1988) Deletion of DNA sequences flanking an Mr 19,000 zein gene reduces its transcriptional activity in heterologous plant tissues. Mol. Gen. Genet. 211, 202-209.

Russell, D. A. and Fromm, M. E. (1997) Tissue-specific expression in transgenic maize of four endosperm promoters from maize and rice. Transgenic Res. 6, 157-168.

Sambrook, J., Fritsch, E. F. and Maniatis, T. (1989) Molecular Cloning: A Laboratory Manual, 2nd Edition. Cold Spring Harbor Laboratory Press, Plainview, N.Y.

Smith, T. F. and Waterman, M. S. (1981) Adv. Appl. Math. 2, 482-489.

Stacey, J. and Issac, P. G. (1994) Isolation of DNA from plants. Methods Mol. Biol. 28, 9-15.

Sprague, G. F. (1946) Early testing of inbred lines of maize. J. Amer. Soc. Agron. 38, 108-117.

Stiefel, V., Ruiz-Avila, L., Raz, R., Pilar Valles, M., Gomez, J., Pages, M., Martinez-Izquierdo, J. A., Ludevid, M. D., Langdale, J. A., Nelson, T., et al. (1990) Expression of a maize cell wall hydroxyproline-rich glycoprotein gene in early leaf and root vascular differentiation. Plant Cell 2, 785-793.

Streatfield, S. J., Jilka, J. M., Hood, E. E., Turner, D. D., Bailey, M. R., Mayor, J. M., Woodard, S. L., Beifuss, K., Horn, M. E., Delaney, D. E., Tizard, I. R. and Howard, J. A. (2001) Plant-based vaccines: unique advantages. Vaccine 19, 2742-2748.

Streatfield, S. J., Mayor, J. M., Barker, D. K., Brooks, C., Lamphear, B. J., Woodard, S. L., Beifuss, K. K., Vicuna, D. V., Massey, L. A. Massey, Horn, M. E., Delaney, D. D., Nikolov, Z. L., Hood, E. E., Jilka, J. M. and Howard, J. A. (2002) Development of an edible subunit vaccine in corn against enterotoxigenic strains of Escherichia coli. In Vitro Cell. Dev. Biol.-Plant 38, 11-17.

Streatfield, S. J., Lane, J. R., Brooks, C. A., Barker, D. K., Poage, M. L., Mayor, J. M., Lamphear, B. J., Drees, C. F., Jilka, J. M., Hood, E. E. and Howard, J. A. (2003) Corn as a production system for human and animal vaccines. Vaccine 21, 812-815.

Takimoto, I., Christensen, A. H., Quail, P. H., Uchimiya, H. and Toki, S. (1994) Non-systemic expression of a stress-response maize polyubiquitin gene (Ubi-1) in transgenic rice plants. Plant Mol. Biol. 26, 1007-1012.

Velten, J. and Schell, J. (1985) Selection-expression plasmid vectors for use in genetic transformation of higher plants. Nucleic Acids Res. 13, 6981-6998.

Vilardell, J., Mundy, J., Stilling, B., Leroux, B., Pla, M., Freyssinet, G. and Pages, M. (1991) Regulation of the maize rab 17 gene promoter in transgenic heterologous systems. Plant Mol. Biol. 17, 985-993.

Wallace, N. H. and Kriz, A. L. (1991) Nucleotide sequence of a cDNA clone corresponding to the maize globulin-2 gene. Plant Physiol. 95, 973-975.

Wan, Y. and Lemaux, P. G. (1994) Generation of large numbers of independently transformed fertile barley plants. Plant Physiol. 104, 37-48.

Waterhouse, P. M., Wang, M. B. and Lough, T. (2001) Gene silencing as an adaptive defense against viruses. Nature 411, 834-842.

Weigel, D. and Nilsson, O. (1995) A developmental switch sufficient for flower initiation in diverse plants. Nature 377, 495-500.

Weising, K., Schell, J. and Kahl, G. (1988) Foreign genes in plants: transfer, structure, expression, and applications. Annu. Rev. Genet. 22, 421-477.

Wohlleben, W., Arnold, W., Broer, I., Hillemann, D., Strauch, E. and Puhler, A. (1988) Nucleotide sequence of the phosphinothricin N-acetyltransferase gene from Streptomyces virochromogenes Tu494 and its expression in Nicotiana tabacum. Gene 70, 25-37.

Woodard, S. L., Mayor, J. M., Bailey, M. R., Barker, D. K., Love, R. T., Lane, J. R., Delaney, D. E., McComas-Wagner, J. M., Mallubhotla, H. D., Hood, E. E., Dangott, L. J., Tichy, S. E. and Howard, J. A. (2003) Maize-derived bovine trypsin: characterization of the first large-scale, commercial protein product from transgenic plants. Biotechnol. Appl. Biochem. 38, 123-130.

Yang, N. S. and Russell, D. (1990) Maize sucrose synthase-1 promoter drives phloem cell-specific expression of GUS gene in transgenic tobacco plants. Proc. Natl. Acad. Sci. USA 87, 4144-4148.

Ye, X., Al-Babili, S., Kloti, A., Zhang, J., Lucca, P., Beyer, P. and Potrykus, I. (2000) Engineering the provitamin A (beta-carotene) biosynthetic pathway into (carotenoid-free) rice endosperm. Science 287, 303-305.

Yu, H. and Kumar, P. P. (2003) Post-transcriptional gene silencing in plants by RNA. Plant Cell Rep. 22, 167-174.

Zhong, G-Y, Peterson, D., Delaney, D. E., Bailey, M., Witcher, D. R., Register, J. C. (III), Bond, D., Li, C-P., Marshall, L., Kulisek, E., Ritland, D., Meyer, T., Hood, E. E. and Howard, J. A. (1999) Commercial production of aprotinin in transgenic maize seeds. Mol. Breed. 5, 345-356.

What is claimed is:

1. An isolated regulatory element that drives transcription of an operably linked heterologous nucleic acid molecule in an embryo-preferred manner, the regulatory element comprising SEQ ID NO: 1 wherein SEQ ID NO:1 is operably linked to said heterologous nucleic acid molecule.

2. An expression cassette comprising a regulatory element that drives transcription of an operably linked heterologous nucleic acid molecule in an embryo-preferred manner, the regulatory element comprising SEQ ID NO: 1 wherein SEQ ID NO:1 is operably linked to said heterologous nucleic acid molecule.

3. A plant, seed, plant embryo or plant cell comprising the expression cassette of claim 2.

4. A method for preferentially expressing a nucleic acid molecule in a plant embryo, the method comprising introducing into at least one plant cell a transformation vector comprising an expression cassette, the expression cassette comprising said nucleic acid molecule operably linked to SEQ ID NO: 1.

5. The regulatory element of claim 1, wherein said element is operably linked to and drives transcription of a nucleic acid molecule such that when introduced into a plant, said nucleic acid molecule is expressed in plant seed at a level of at least 0.1% total soluble protein.

6. The regulatory element of claim 1, wherein said element is operably linked to and drives transcription of a nucleic acid molecule such that when introduced into a plant, said nucleic acid molecules is expressed in plant seed at a level of at least 0.4% total soluble protein.

7. The expression cassette of claim 2, wherein said element is operably linked to and drives transcription of a nucleic acid molecule such that when said cassette is introduced into a plant, said nucleic acid molecules is expressed in seed of said plant at a level of at least 0.1% total soluble protein.

8. The expression cassette of claim 2, wherein said element is operably linked to and drives transcription of a nucleic acid molecule such that when said cassette is introduced into a plant, said nucleic acid molecules is expressed in seed of said plant at a level of at least 0.4% total soluble protein.

9. The plant, seed, embryo or cell of claim 3, wherein said element is operably linked to and drives transcription of a nucleic acid molecule such said nucleic acid molecules is expressed in seed of said plant, said seed, or seed comprising said embryo or cell at a level of at least 0.1% total soluble protein.

10. The plant, seed, embryo or cell of claim 3, wherein said element is operably linked to and drives transcription of a nucleic acid molecule such that said nucleic acid molecule is expressed in seed of said plant, said seed, or seed comprising said embryo or cell at a level of at least 0.4% total soluble protein.

11. The method of claim 4, wherein said method further comprises producing a plant comprising said transformation vector, wherein said plant expresses said nucleic acid molecule in seed of said plant at a level of at least 0.1% total soluble protein.

12. The method of claim 4, wherein said method further comprises producing a plant comprising said transformation vector, wherein said plant expresses said nucleic acid molecule in seed of said plant at a level of at least 0.4% total soluble protein.

13. The method of claim 4, wherein said method further comprises producing a plant and determining if the expression level of said nucleic acid molecule in seed of said plant is at least 0.1% total soluble protein.

14. The method of claim 13, wherein said expression level is determined to be at least 0.4% total soluble protein.

15. The method of claim 4, wherein said method further comprises producing a plant, determining the expression level of said nucleic acid molecule in seed of said plant and selecting said plant or seed if expression of said nucleic acid molecule is at least 0.1% total soluble protein.

16. The method of claim 4, wherein said method further comprises producing a plant, determining the expression level of said nucleic acid molecule in seed of said plant such that when said plant is operably linked to a nucleic acid molecule encoding a protein, said protein is expressed at levels of at least 0.1% total soluble protein.

* * * * *

SEQUENCE LISTING

```
<160> NUMBER OF SEQ ID NOS: 2

<210> SEQ ID NO 1
<211> LENGTH: 2987
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
```

```
tcctcctgct cccctcctac ctctggtgga ccatcgaccg cgcccggctc cggtgcctgc      60
accgcacgcc acatgcggcc gatgggcagc ggaagctagc agcccggctt gaatgaccta     120
tattatatga agaagatgcc tcagatgcta ctcgactaca aggtttatgt ttctcaggtg     180
actaaataga tcatgtgctg atgttagcga ttccttgtgtg gaagtgaatt catgccaatt   240
tgaagccaat atggtttagg tgtatttttt actggattta ggttgaaggt caatttgtct     300 tcttttatt ctgcaaatac acattgacaa cctaatgact ttctattgtt ttaatatcag      360
accaataaac cttttttctt tttttaatat gctatgaact gtatcagctt tgtgacctct     420
tgtttccatt tccccttgga ttcatataat taactttcga caccagagca atacatctgt    480
catcaattat taacataata tgttatgtct tgcttggttt agcctcaaga ggttttatgc     540
atgttctttt gtattgcttg gggtgttaac ttttttatc catttggtgt gggtgagggt      600
gggatctgtt attcctgatg taatgcataa tccattcatt atgatcatag taggaatatg    660
gctacactga ctctttcttc ctcagtggag tacaattggt ggccttatat acttgatgtg     720
ggcgtcattt ttacgattgc ctctgaatgt gggagtagtc ttatggtaat aaaagtcaaa     780
caattctaat gtgttgtgct agatctaaat taccttgaag acattgttgg gggttccaat     840
gtcactgttg acatcatatc caaatttgta tccttctgta tggtgtgata tatctagaag    900
ctctaagaat ttttgtcttg tgcaggtcct gtaattaatg aatgatttga accaaagtgt    960
tcgaggtact gttctcttgt attgaggtta gttaattcca tatttgatac tctataggcc   1020
tactttagtt gacattttga ttttttccac acccataatg actggtgtga tatctatttc    1080
cattgatctt gttcaatttc ccaatagtta catcctacat ttacaacctg gagagattga    1140
agcattttta tagcaacatc tgaactatta aaactcaccg tttgctccac cacgggctta    1200
ggttcttcga cctctctatg aatcccccta agataccaga actgttgtag tggttatata    1260
tattgagtat ctgtttgaat tgtaagacct tgtgatattt ccagaagatt tgtataagtc    1320
tgtaatttgt tgtgataata ttagcatcta aatgatgcaa ttgatataac attattaaaa   1380
tcataaatag aagtttgcat ggtaccgatg gttgcaatgt agtggtgaaa taactatatt    1440
aaaataacaa aatgtatgta tggctagcta ggatttataa aatcttttc ttataacaca     1500 tatttgtata taaattatca tgatattata tgttcccgtt gcaacgcacg ggcacttata    1560
tatatatatg tgtgtgtttt tttttcaca tgtacccatc agataggatg ataagagagg     1620
ttaaatcatg ccttaaggaa catcttaaga agtgttttta catgctacat tttggtggat   1680
tttatataac cgttttttac atacatacgg ccctatatat atcatagttc agtttgattc    1740
ctccgttaca aaccaactaa atgcatagac cacgcggacc gaaagcaaca gggtcgatga    1800
gtcgaagcag cggggccgat gaagtcgaag cggtctcctg aacgcagatg cacgtcggcg    1860
atcgggatgg ctgggatggc gacgcagttg tgagtagagg cgaaaactta atttgtgttg    1920
ggattgacac taggcgccct atatagggcc gtgtccacga accgataacg atgcgcgatc    1980
cgatctacac gttatccacg aatcgataga ctcgcgttcc gttcatatcc ttatcgggat    2040
cggttagggc tctaaaatta acagccaagc aacagcctcg gcccggcgag gcgagcgcgt    2100
gtggttctcc acactctctc ctctcatcca tgacttggtg agtgagcgta gcatccatat    2160
ttaaactagt tccactccac ttgaactagc aatatgacac tatttgtttc accattctct    2220
agccatacca tacatgcgct tttgagattt ttttaggatt taattgaatt tctcaattgg    2280
gcctatccca taaatccaac acgatataag tctatctgtc gctggtagat tgagagatga    2340
tgtgtgcatg tctgtaaata aaaaaaattg cttttacaca taaattgcgc tatgacttta    2400
```

-continued

| | |
|---|---|
| catgaaataa attttctaaa atttaaaact tacataagta aaaaaaatat aaagaaggaa | 2460 |
| gaaacacgac atggaaaaaa aatctctcgt tgttttatat ggaggcaacg gctgcagtcc | 2520 |
| ccgtgcaagc gatgctcatc cgttcccatg gcgtgcacgg cccagaaacg acacgcttca | 2580 |
| cctacttctt ccctgccacc acacccaccg tccacccaca ccacaccgcg cgccacgcgc | 2640 |
| ccacggcacc tcggcacagt gtcgtcgcat gtcgctcacg tactgtcgca gaactcacac | 2700 |
| cgtcacacgg tgcctgctat ctagctaatg ctgctagcag ccatgtcaca ccgatataac | 2760 |
| ccggccaccg cgcgccgcgc cacgtcgcca tgcacgcggc cacgtccccg atcgatcgac | 2820 |
| gtcgtcctcc tcatcctggc tcctccattc ccgcgcttct ataaataccct cggccatgta | 2880 |
| catcgaccca gccatctcct caccctcgtt caccacacag cccgccactc ctttagtagc | 2940 |
| ttgtgatttg tacgtcgacg agatcactgg ttggcggacg acgaccc | 2987 |

<210> SEQ ID NO 2
<211> LENGTH: 2990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | |
|---|---|
| tcctcctgct cccctcctac ctctggtgga ccatcgaccg cgcccggctc cggtgcctgc | 60 |
| accgcacgcc acatgcggcc gatgggcagc ggaagctagc agcccggctt gaatgaccta | 120 |
| tattatatga agaagatgcc tcagatgcta ctcgactaca aggtttatgt ttctcaggtg | 180 |
| actaaataga tcatgtgctg atgttagcga ttcttgtgtg gaagtgaatt catgccaatt | 240 |
| tgaagccaat atggtttagg tgtattttt actggattta ggttgaaggt caatttgtct | 300 |
| tcttttatt ctgcaaatac acattgacaa cctaatgact ttctattgtt ttaatatcag | 360 |
| accaataaac cttttttctt ttttaatat gctatgaact gtatcagctt tgtgacctct | 420 |
| tgtttccatt tccccttgga ttcatataat taactttcga caccagagca atacatctgt | 480 |
| catcaattat taacataata tgttatgtct tgcttggttt agcctcaaga ggttttatgc | 540 |
| atgttctttt gtattgcttg gggtgttaac ttttttttatc catttggtgt gggtgagggt | 600 |
| gggatctgtt attcctgatg taatgcataa tccattcatt atgatcatag taggaatatg | 660 |
| gctacactga ctctttcttc ctcagtggag tacaattggt ggccttatat acttgatgtg | 720 |
| ggcgtcattt ttacgattgc ctctgaatgt gggagtagtc ttatggtaat aaaagtcaaa | 780 |
| caattctaat gtgttgtgct agatctaaat taccttgaag acattgttgg gggttccaat | 840 |
| gtcactgttg acatcatatc caaatttgta tccttctgta tggtgtgata tatctagaag | 900 |
| ctctaagaat ttttgtcttg tgcaggtcct gtaattaatg aatgatttga accaaagtgt | 960 |
| tcgaggtact gttctcttgt attgaggtta gttaattcca tatttgatac tctataggcc | 1020 |
| tactttagtt gacattttga ttttttccac acccataatg actggtgtga tatctatttc | 1080 |
| cattgatctt gttcaatttc ccaatagtta catcctacat ttacaacctg gagagattga | 1140 |
| agcatttta tagcaacatc tgaactatta aaactcaccg tttgctccac cacgggctta | 1200 |
| ggttcttcga cctctctatg aatcccccta agataccaga actgttgtag tggttatata | 1260 |
| tattgagtat ctgtttgaat tgtaagacct tgtgatattt ccagaagatt tgtataagtc | 1320 |
| tgtaatttgt tgtgataata ttagcatcta aatgatgcaa ttgatataac attattaaaa | 1380 |
| tcataaatag aagtttgcat ggtaccgatg gttgcaatgt agtggtgaaa taactatatt | 1440 |
| aaaataacaa aatgtatgta tggctagcta ggatttataa aatctttttc ttataacaca | 1500 |

```
tatttgtata taaattatca tgatattata tgttcccgtt gcaacgcacg ggcacttata    1560
tatatatatg tgtgtgtttt tttttcaca tgtacccatc agataggatg ataagagagg    1620
ttaaatcatg ccttaaggaa catcttaaga agtgttttta catgctacat tttggtggat    1680
tttatataac cgttttttac atacatacgg ccctatatat atcatagttc agtttgattc    1740
ctccgttaca aaccaactaa atgcatagac cacgcggacc gaaagcaaca gggtcgatga    1800
gtcgaagcag cggggccgat gaagtcgaag cggtctcctg aacgcagatg cacgtcggcg    1860
atcgggatgg ctgggatggc gacgcagttg tgagtagagg cgaaaactta atttgtgttg    1920
ggattgacac taggcgcctt atatagggcc gtgtccacga accgataacg atgcgcgatc    1980
cgatctacac gttatccacg aatcgataga ctcgcgttcc gttcatatcc ttatcgggat    2040
cggttagggc tctaaaatta acagccaagc aacagcctcg gcccggcgag gcgagcgcgt    2100
gtggttctcc acactctctc ctctcatcca tgacttggtg agtgagcgta gcatccatat    2160
ttaaactagt tccactccac ttgaactagc aatatgacac tatttgtttc accattctct    2220
agccatacca tacatgcgct tttgagattt ttttaggatt taattgaatt tctcaattgg    2280
gcctatccca taaatccaac acgatataag tctatctgtc gctggtagat tgagagatga    2340
tgtgtgcatg tctgtaaata aaaaaaattg cttttacaca taaattgcgc tatgacttta    2400
catgaaataa attttctaaa atttaaaact tacataagta aaaaaaatat aaagaaggaa    2460
gaaacacgac atggaaaaaa aatctctcgt tgttttatat ggaggcaacg gctgcagtcc    2520
ccgtgcaagc gatgctcatc cgttcccatg gcgtgcacgg cccagaaacg acacgcttca    2580
cctacttctt ccctgccacc acacccaccg tccacccaca ccacaccgcg cgccacgcgc    2640
ccacggcacc tcggcacagt gtcgtcgcat gtcgctcacg tactgtcgca gaactcacac    2700
cgtcacacgg tgcctgctat ctagctaatg ctgctagcag ccatgtcaca ccgatataac    2760
ccggccaccg cgcgccgcgc cacgtcgcca tgcacgcggc cacgtccccg atcgatcgac    2820
gtcgtcctcc tcatcctggc tcctccattc ccgcgcttct ataaatacct cggccatgta    2880
catcgaccca gccatctcct caccctcgtt caccacacag cccgccactc ctttagtagc    2940
ttgtgatttg tacgtcgacg agatcactgg ttggcggacg acgacccatg             2990
```